United States Patent
Jang et al.

(10) Patent No.: US 12,040,046 B2
(45) Date of Patent: Jul. 16, 2024

(54) OPERATING METHOD OF MEMORY DEVICE FOR EXTENDING SYNCHRONIZATION OF DATA CLOCK SIGNAL, AND OPERATING METHOD OF ELECTRONIC DEVICE INCLUDING THE SAME

(71) Applicant: SAMSUNG ELECTRONICS CO., LTD., Suwon-si (KR)

(72) Inventors: Jin-Hoon Jang, Uiwang-si (KR); Kyungryun Kim, Seoul (KR); Young Ju Kim, Suwon-si (KR); Seung-Jun Lee, Hwaseong-si (KR); Youngbin Lee, Seoul (KR); Yeonkyu Choi, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 18/447,950

(22) Filed: Aug. 10, 2023

(65) Prior Publication Data
US 2023/0386542 A1 Nov. 30, 2023

Related U.S. Application Data

(63) Continuation of application No. 17/496,003, filed on Oct. 7, 2021, now Pat. No. 11,783,880.

(30) Foreign Application Priority Data

Mar. 9, 2021 (KR) .................. 10-2021-0030656

(51) Int. Cl.
*G11C 8/18* (2006.01)
*G11C 7/10* (2006.01)

(52) U.S. Cl.
CPC .............. *G11C 8/18* (2013.01); *G11C 7/1045* (2013.01); *G11C 7/1066* (2013.01); *G11C 7/1093* (2013.01)

(58) Field of Classification Search
CPC ....................................................... G11C 8/18
(Continued)

(56) References Cited

U.S. PATENT DOCUMENTS 7,889,595 B2   2/2011   Park
8,125,251 B2   2/2012   Park
(Continued)

FOREIGN PATENT DOCUMENTS

TW        200534098        10/2005

OTHER PUBLICATIONS

Notice Of Allowance dated May 25, 2023 in corresponding U.S. Appl. No. 17/496,003.
(Continued)

*Primary Examiner* — Muna A Techane
(74) *Attorney, Agent, or Firm* — F, Chau & Associates, LLC

(57) ABSTRACT

Disclosed is an operating method of a memory device communicating with a memory controller, which includes receiving a first command from the memory controller, the first command indicating initiation of synchronization of a data clock signal and defining a clock section corresponding to the synchronization, preparing a toggling of the data clock signal during a preparation time period, processing a first data stream based on the data clock signal toggling at a reference frequency, and processing a second data stream based on the data clock toggling at the reference frequency and extended for a period of the defined first clock section.

20 Claims, 22 Drawing Sheets

(58) Field of Classification Search
USPC .................................................... 365/233.1
See application file for complete search history.

(56) References Cited

U.S. PATENT DOCUMENTS

| | | | |
|---|---|---|---|
| 8,130,890 B2 | 3/2012 | Kim et al. | |
| 8,242,819 B2 | 8/2012 | Bae et al. | |
| 8,687,457 B2 | 4/2014 | Park | |
| 8,693,603 B2 | 4/2014 | Kim et al. | |
| 10,559,550 B2 | 2/2020 | Lee et al. | |
| 10,692,554 B2 | 6/2020 | Son et al. | |
| 2006/0077736 A1* | 4/2006 | Nakagawa | G11C 29/50004 365/201 |
| 2007/0248047 A1 | 10/2007 | Shorty et al. | |
| 2009/0168564 A1* | 7/2009 | Lee | G11C 7/109 365/194 |
| 2013/0155791 A1* | 6/2013 | Ok | G11C 7/22 365/189.16 |
| 2016/0336058 A1* | 11/2016 | Song | G11C 7/109 |
| 2017/0004869 A1* | 1/2017 | Shin | G11C 11/4096 |
| 2018/0124687 A1 | 5/2018 | Park et al. | |
| 2019/0163652 A1* | 5/2019 | Kim | G11C 29/023 |
| 2019/0172512 A1* | 6/2019 | Oh | G11C 29/1201 |
| 2019/0230706 A1 | 7/2019 | Li et al. | |
| 2020/0133505 A1 | 4/2020 | Kim | |
| 2022/0293154 A1 | 9/2022 | Jang et al. | |

OTHER PUBLICATIONS

Office Action dated Feb. 2, 2023 in corresponding U.S. Appl. No. 17/496,003.

* cited by examiner

OPERATING METHOD OF MEMORY DEVICE FOR EXTENDING SYNCHRONIZATION OF DATA CLOCK SIGNAL, AND OPERATING METHOD OF ELECTRONIC DEVICE INCLUDING THE SAME

CROSS-REFERENCE TO RELATED APPLICATIONS

This non-provisional patent application is a continuation of U.S. patent application Ser. No. 17/496,003 filed Oct. 7, 2021, which claims priority under 35 U.S.C. § 119 to Korean Patent Application No. 10-2021-0030656 filed on Mar. 9, 2021, in the Korean Intellectual Property Office, the disclosures of which are incorporated by reference in their entirety herein.

1. TECHNICAL FIELD

Embodiments of the present disclosure described herein relate to an operating method of a memory device, and more particularly, relate to an operating method of a memory device for extending synchronization of a data clock signal, and an operating method of an electronic device including the memory device.

2. DISCUSSION OF RELATED ART

A memory device may include various circuits for generating, processing, or storing data. For example, the memory device may include various circuits for storing or outputting data based on electrical signals such as a command, an address, a clock signal, a data clock signal, and data. The data clock signal may be directly involved in storing or outputting data, and a frequency of the data clock signal may be higher than a frequency of a clock signal.

As the amount of data to be processed in the memory device increases, the frequency of the data clock signal may increase, thereby causing an increase in power consumption of the memory device. To reduce power consumption, the memory device may selectively enable synchronization of the data clock signal. When data processing has completed, the synchronization of the data clock signal is disabled, and the memory device again enables the synchronization of the data clock signal for the purpose of processing next data. However, since it takes time to again enable synchronization of the data clock signal, a next data processing is delayed.

SUMMARY

At least one embodiment of the present disclosure provides an operating method of a memory device for extending synchronization of a data clock signal, and an operating method of an electronic device including the memory device.

According to an embodiment, an operating method of a memory device which communicates with a memory controller includes receiving a first command from the memory controller, the first command indicating initiation of synchronization of a data clock signal and defining a clock section corresponding to the synchronization, preparing a toggling of the data clock signal during a preparation time period, processing a first data stream based on the data clock signal toggling at a reference frequency, and processing a second data stream based on the data clock signal toggling at the reference frequency and extended for a period of the defined clock section.

According to an embodiment, an operating method of a memory device which communicates with a memory controller includes receiving a first command and a second command from the memory controller, the first command including mode register setting information and the second command indicating initiation of synchronization of a data clock signal, changing settings of a mode register based on the mode register setting information, preparing a toggling of the data clock signal during a preparation time period, processing a first data stream based on the data clock signal toggling at a reference frequency, and processing a second data stream based on the data clock signal toggling at the reference frequency and extended according to a reference cycle count of the changed settings.

According to an embodiment, an operating method of an electronic device which includes a memory device and a memory controller controlling the memory device includes providing, by the memory controller, a command for extending a synchronization of a data clock signal, preparing, by the memory device, a toggling of the data clock signal during a preparation time period, processing, by the memory device, a first data stream based on the data clock signal toggling at a reference frequency, and processing, by the memory device, a second data stream based on the data clock signal toggling at the reference frequency, and the synchronization of the data clock signal is extended based on the command.

According to an embodiment, an operating method of an electronic device which includes a memory device and a memory controller controlling the memory device includes determining, by the memory controller, whether a processing interval between a first processing command and a second processing command is shorter than a reference interval, when it is determined that the processing interval is shorter than the reference interval, generating, by the memory controller, an extension command for extending a synchronization of a data clock signal, preparing, by the memory device, a toggling of the data clock signal during a preparation time period based on the extension command, processing, by the memory device, a first data stream corresponding to the first processing command based on the data clock signal toggling at a reference frequency, and processing, by the memory device, a second data stream corresponding to the second processing command based on the data clock signal toggling at the reference frequency, and the synchronization of the data clock signal is extended based on the extension command.

BRIEF DESCRIPTION OF THE FIGURES

The above and other objects and features of the present disclosure will become apparent by describing in detail embodiments thereof with reference to the accompanying drawings.

DETAILED DESCRIPTION

Figure 1:
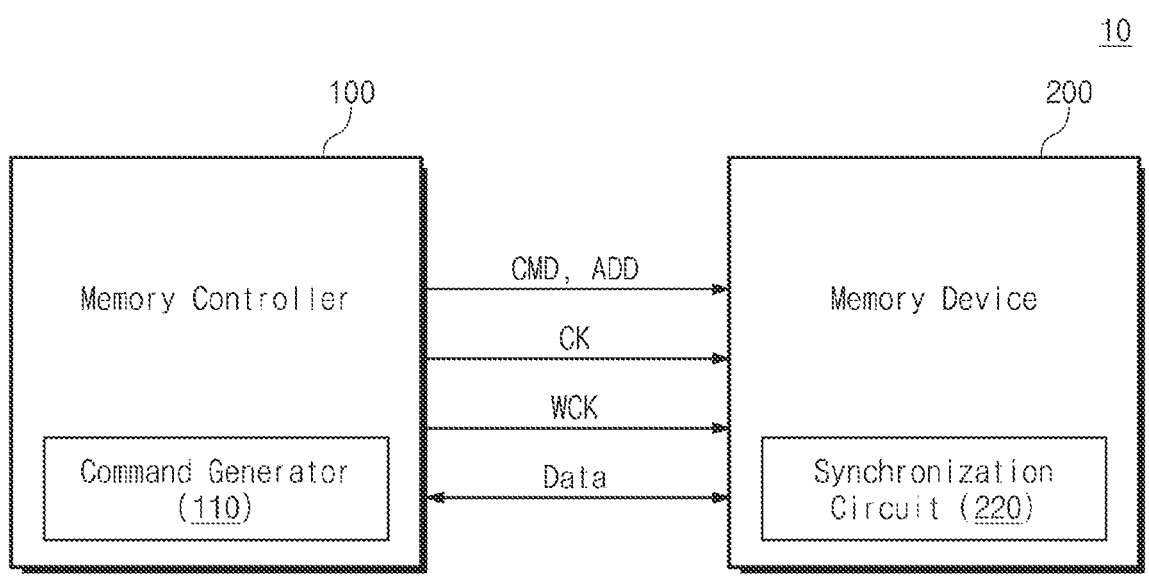
FIG. 1 is a block diagram illustrating an electronic device according to an embodiment of the present disclosure.

Below, embodiments of the present disclosure will be described in detail and clearly to such an extent that one skilled in the art may implement the present disclosure. Below, for convenience of description, like components are expressed by using the same or like reference numerals.

FIG. 1 is a block diagram illustrating an electronic device according to an embodiment of the present disclosure. Referring to FIG. 1, an electronic device 10 includes a memory controller 100 (e.g., a control circuit) and a memory device 200. The electronic device 10 may be a device that stores data or outputs the stored data. For example, the electronic device 10 may be used to store data in the following devices: a computer, a tablet, a laptop, a notebook computer, a personal digital assistant (PDA), a mobile computing device, a smartphone, and an Internet home appliance.

The memory controller 100 may communicate with the memory device 200. The memory controller 100 may control the memory device 200. The memory controller 100 may store data in the memory device 200 or may read data stored in the memory device 200. The memory controller 100 may include a command generator 110 (e.g., a circuit). The command generator 110 may generate a command CMD.

The memory controller 100 may generate the command CMD, an address ADD, a clock signal CK, and a data clock signal WCK. The memory controller 100 may output the command CMD, the address ADD, the clock signal CK, and the data clock signal WCK to the memory device 200. The memory controller 100 may output data to the memory device 200 or may receive the data from the memory device 200.

The memory device 200 may receive the command CMD, the address ADD, the clock signal CK, and the data clock signal WCK from the memory controller 100. The memory device 200 may output the data to the memory controller 100 or may receive the data from the memory controller 100. That is, the memory device 200 may be a device that stores data. For example, the memory device 200 may be volatile memory such as a dynamic random access memory (DRAM), a synchronous DRAM (SDRAM), or a static random access memory (SRAM), but the present disclosure is not limited thereto.

The memory device 200 may include a synchronization circuit 220. The synchronization circuit 220 may control synchronization of the data clock signal WCK. The synchronization of the data clock signal WCK may mean that the data clock signal WCK toggles at a timing synchronized with the clock signal CK for the purpose of reading or writing data. The toggling may mean that a logical state transitions from low (L) to high (H) or transitions from H to L.

The command CMD may be a signal indicating an operation to be performed by the memory device 200. For example, the command CMD may include read, write, refresh, precharge, mode register, column address strobe CAS, deselect DES, etc., but the present disclosure is not limited thereto. For example, the command CMD may vary depending on the specification that is applied to the memory device 200.

In an embodiment, the CAS that is a command accompanied before the read command or the write command may be a command for initiating the synchronization of the data clock signal WCK in the LPDDR5 (Low Power Double Data Rate 5). In an embodiment, the DES may be a command indicating that the memory device 200 is to perform no operation.

In an embodiment, the memory controller 100 may be connected with the memory device 200 through a command/address bus (i.e., a CA bus) including a plurality of command pins. The memory controller 100 may output command/address signals (hereinafter referred to as "CAs") to the plurality of command pins of the CA bus, and a combination of the CAs may correspond to the command CMD or the address ADD. The memory device 200 may determine the command CMD based on the CAs received through the plurality of command pins and a command truth table.

In an embodiment, the command generator 110 generates a command defined by a user. In an embodiment, the command generator 110 generates a command for changing settings (e.g., mode register settings) of the memory device 200. This will be described in more detail with reference to FIG. 2.

The address ADD may be a signal indicating a location of a memory rank, a memory bank, a memory cell, etc. of the memory device 200, at which an operation is to be performed. For example, the address ADD may include a row address and a column address of a memory cell of a memory bank in a selected memory rank.

The clock signal CK may be a signal that toggles periodically. For example, the clock signal CK may be an electrical signal having a logical high level and a logical low level that are periodically repeated. The clock signal CK may be used to determine a timing being a reference of communication with the memory device 200 or an internal operation of the memory device 200. In an embodiment, the clock signal CK includes complementary clock signals CK_t and CK_c.

The data clock signal WCK may be a signal that is used in reading or writing data. A frequency of the data clock signal WCK may be higher than a frequency of the clock signal CK. For example, the data clock signal WCK may be a signal that toggles at a high frequency for data processing. In an embodiment, the data clock signal WCK includes complementary clock signals WCK_t and WCK_c.

In an embodiment, to reduce power consumption of the memory device 200, the synchronization circuit 220 temporarily performs synchronization of the data clock signal WCK only when a request is received from the memory controller 100. After a given time period passes, the synchronization of the data clock signal WCK may be disabled. In the case where there is a need to process next data, the synchronization circuit 220 may again perform synchronization of the data clock signal WCK depending on the request of the memory controller 100. This will be described in more detail with reference to FIG. 3.

In an embodiment, the memory controller 100 and the memory device 200 exchange data with each other. For example, when the command CMD is the write command, the memory controller 100 may output data to the memory device 200. For example, when the command CMD is the read command, the memory controller 100 may receive data from the memory device 200. The data may be at least a portion of a computer program or application, or may be at least a portion of user data such as an image, a video, a voice, or a text. In an embodiment, the communication between the memory controller 100 and the memory device 200 may comply with the specification defined in the LPDDR5.

Figure 2:
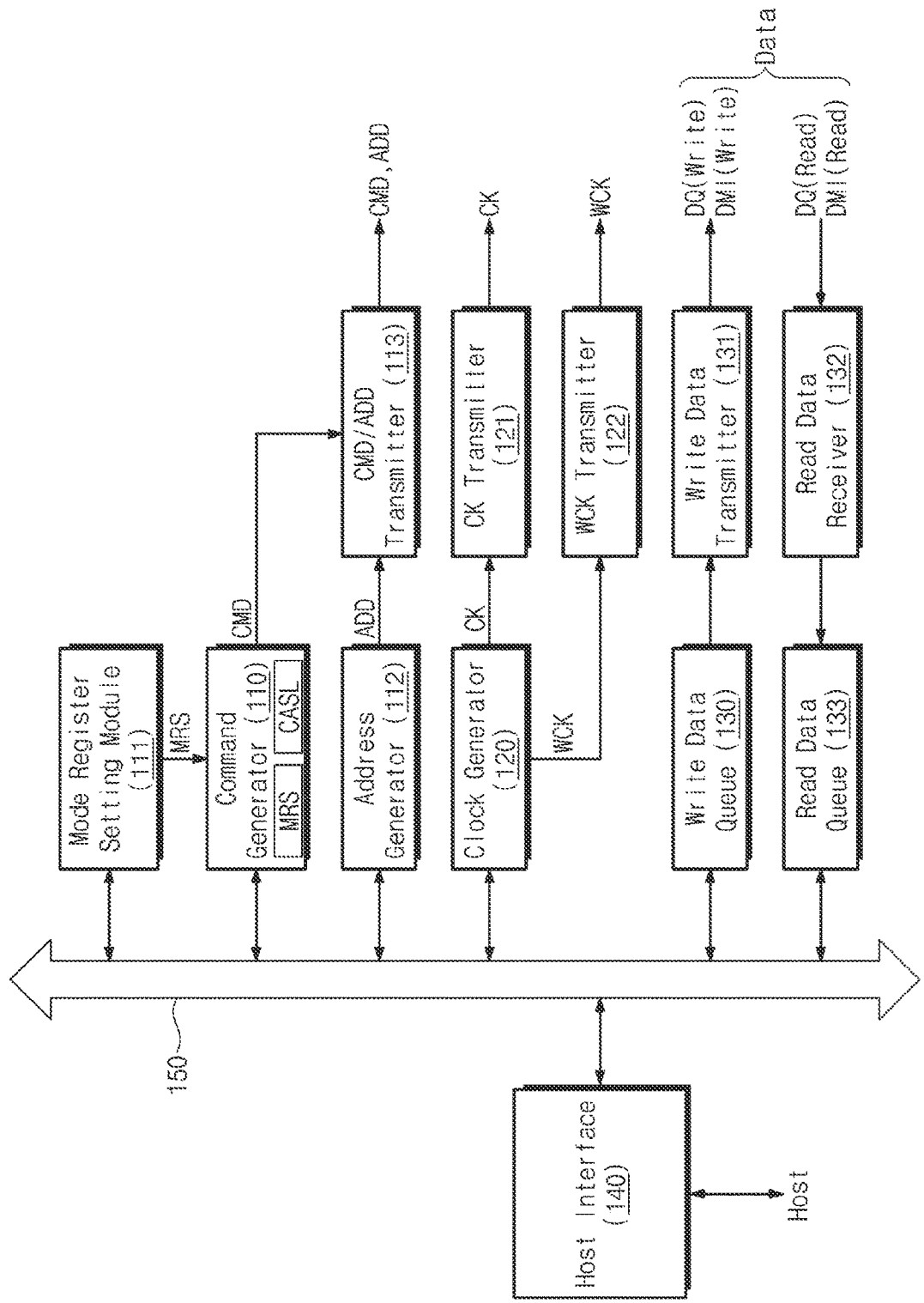
FIG. 2 is a block diagram illustrating a memory controller of FIG. 1, according to an embodiment of the present disclosure.

FIG. 2 is a block diagram illustrating a memory controller of FIG. 1, according to an embodiment of the present disclosure. Referring to FIGS. 1 and 2, the memory controller 100 may communicate with a host and the memory device 200. For example, the memory controller 100 may output the command CMD, the address ADD, the clock signal CK, and the data clock signal WCK to the memory device 200 and may communicate with the memory device 200.

The memory controller 100 may include the command generator 110, a mode register setting module 111 (e.g., a circuit), an address generator 112 (e.g., a circuit), a CMD/ADD transmitter 113, a clock generator 120 (e.g., a signal generator), a CK transmitter 121, a WCK transmitter 122, a write data queue 130, a write data transmitter 131, a read data receiver 132, a read data queue 133, a host interface 140 (e.g., an interface circuit), and a bus 150.

The command generator 110 may generate the command CMD. The command generator 110 may output the command CMD to the CMD/ADD transmitter 113.

In an embodiments, the command generator 110 generates a column address strobe lengthened CASL, which is defined by the user, based on communication with the host and outputs the command CMD including the CASL. The CASL may be a command that is similar to the CAS in terms of initiating the synchronization of the data clock signal WCK but is defined independently of the CAS to extend the synchronization of the data clock signal WCK. The CASL will be described in more detail with reference to FIGS. 5 and 6 together.

In an embodiment, the command generator 110 receives mode register setting information MRS from the mode register setting module 111. The command generator 110 may output a command CMD including the mode register setting information MRS. The mode register setting information MRS may be information for changing mode register settings of the memory device 200. The mode register setting information MRS will be described in more detail with reference to FIGS. 7 and 8 together.

The mode register setting module 111 may generate the mode register setting information MRS defined by the user, based on communication with the host. The mode register setting module 111 may output the mode register setting information MRS to the command generator 110.

The address generator 112 may generate the address ADD. The address generator 112 may output the address ADD to the CMD/ADD transmitter 113. The CMD/ADD transmitter 113 may receive the command CMD from the command generator 110. The CMD/ADD transmitter 113 may receive the address ADD from the address generator 112. The CMD/ADD transmitter 113 may output the command CMD and the address ADD to the memory device 200.

The clock generator 120 may generate the clock signal CK and the data clock signal WCK. The clock generator 120 may output the clock signal CK to the CK transmitter 121. The clock generator 120 may output the data clock signal WCK to the WCK transmitter 122. The CK transmitter 121 may output the clock signal CK to the memory device 200. The WCK transmitter 122 may output the data clock signal WCK to the memory device 200.

The write data queue 130 may store data to be written in the memory device 200. For example, data stored in the write data queue 130 may be data provided from the host. The write data queue 130 may output the data to the write data transmitter 131. The write data transmitter 131 may output the data to the memory device 200. For example, the write data transmitter 131 may output, to the memory device 200, a data signal DQ and a data mask inversion signal DMI for a write operation. The data signal DQ may be a signal indicating actual information of data. The data mask inversion signal DMI may be a signal for data mask and data bus inversion.

The read data receiver 132 may receive data from the memory device 200. For example, the read data receiver 132 may receive the data signal DQ and the data mask inversion signal DMI for a read operation from the memory device 200. The read data receiver 132 may output the data to the read data queue 133. The read data queue 133 may store the data read from the memory device 200. The read data queue 133 may provide the host with the data corresponding to a request (e.g., a read request) of the host.

The host interface 140 may communicate with the host. The host interface 140 may receive the mode register setting information MRS and the CASL from the host and may output the mode register setting information MRS and the CASL to the command generator 110. The host interface 140 may receive data for the write operation from the host and may output the data to the write data queue 130. The host interface 140 may receive data associated with the read operation from the read data queue 133 and may output the data to the host.

The bus 150 may electrically connect the command generator 110, the mode register setting module 111, the address generator 112, the CMD/ADD transmitter 113, the clock generator 120, the CK transmitter 121, the WCK transmitter 122, the write data queue 130, the write data transmitter 131, the read data receiver 132, the read data queue 133, and the host interface 140.

Figure 3:
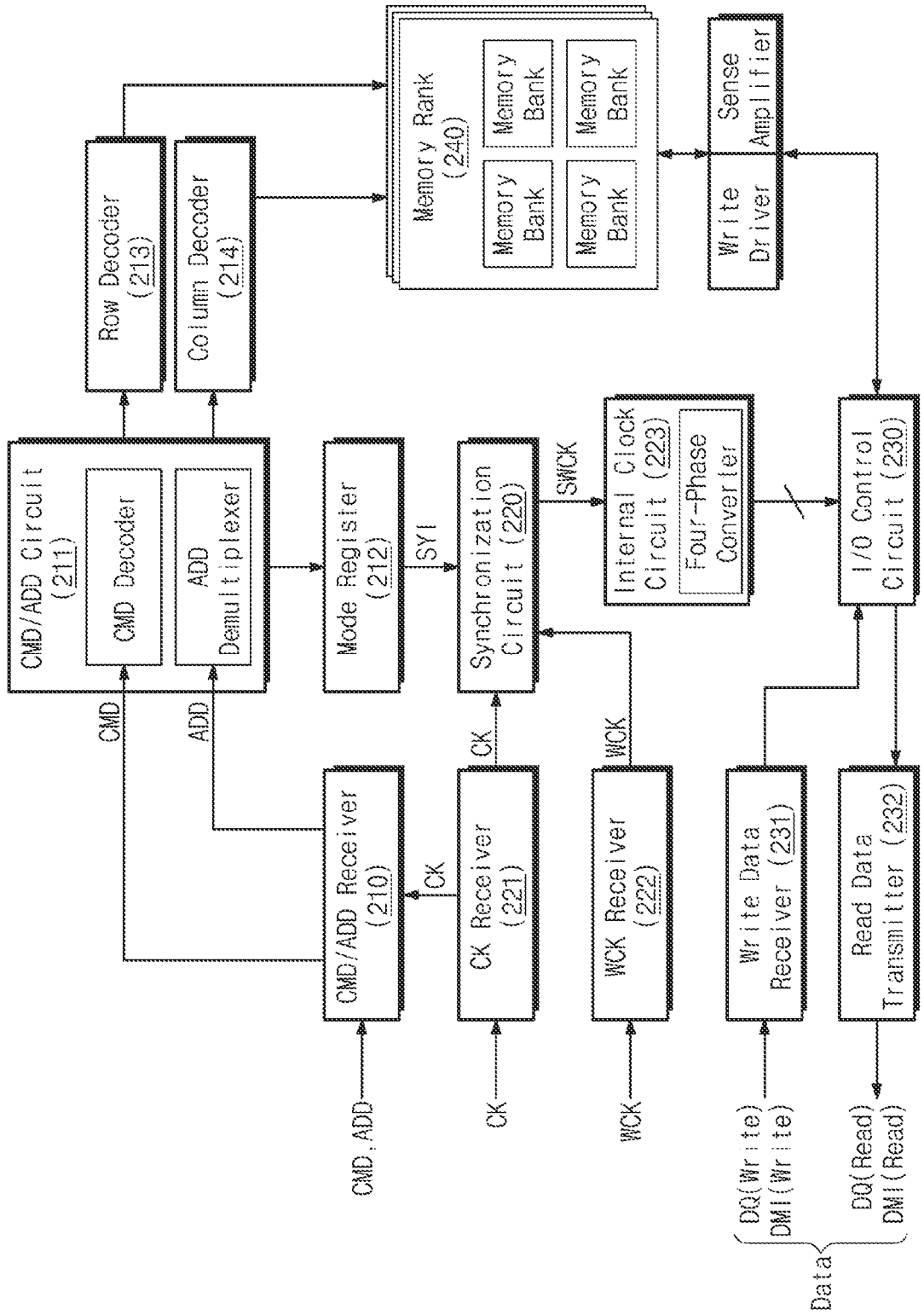
FIG. 3 is a block diagram illustrating a memory device of FIG. 1, according to an embodiment of the present disclosure.

FIG. 3 is a block diagram illustrating a memory device of FIG. 1, according to an embodiment of the present disclosure. Referring to FIGS. 1 and 3, the memory device 200 may communicate with the memory controller 100. For example, the memory device 200 may receive the command CMD, the address ADD, the clock signal CK, and the data clock signal WCK from the memory controller 100 and may communicate with the memory controller 100.

The memory device 200 includes a CMD/ADD receiver 210, a CMD/ADD circuit 211, a mode register 212, a row decoder 213 (e.g., a decoder circuit), a column decoder 214 (e.g., a decoder circuit), the synchronization circuit 220, a CK receiver 221, a WCK receiver 222, an internal clock circuit 223, an input/output (I/O) control circuit 230, a write data receiver 231, a read data transmitter 232, and a plurality of memory ranks 240.

The CMD/ADD receiver 210 may receive the command CMD and the address ADD from the memory controller 100 through the CA bus. The CMD/ADD receiver 210 may receive the clock signal CK from the CK receiver 221. The CMD/ADD receiver 210 may output the command CMD and the address ADD to the CMD/ADD circuit 211.

The CMD/ADD circuit 211 may include a CMD decoder (e.g., a decoder circuit) and an ADD demultiplexer. The CMD decoder may decode the command CMD. The ADD demultiplexer may demultiplex the address ADD. The CMD/ADD circuit 211 may control the mode register 212 based on a decoding result of the CMD decoder.

In an embodiment, when the command CMD is determined as the CAS by the CMD decoder, the CMD/ADD circuit 211 controls the mode register 212 or the synchronization circuit 220 to initiate synchronization. In an embodiment, when the decoding result of the CMD decoder indicates that the command CMD includes the mode register setting information MRS, the CMD/ADD circuit 211 changes settings of the mode register 212.

The CMD/ADD circuit 211 may control the row decoder 213 and the column decoder 214 based on a demultiplexing result of the ADD demultiplexer. For example, the ADD demultiplexer may demultiplex the address ADD to obtain a row address and a column address. The CMD/ADD circuit 211 may output the row address to the row decoder 213. The CMD/ADD circuit 211 may output the column address to the column decoder 214.

The mode register 212 may be connected with the CMD/ADD circuit 211. In an embodiment, settings of the mode register 212 may be changed based on the mode register setting information MRS decoded by the CMD/ADD circuit 211. In an embodiment, the mode register 212 outputs a synchronization initiation signal SYI to the synchronization circuit 220 under control of the CMD/ADD circuit 211. The synchronization initiation signal SYI may be a signal that triggers the synchronization of the data clock signal WCK.

The row decoder 213 may be connected to the plurality of memory ranks 240. The column decoder 214 may be connected to the plurality of memory ranks 240. A location of a memory cell in the plurality of memory ranks 240 may be specified by the row decoder 213 and the column decoder 214. For example, the row decoder 213 may specify a row of a memory rank based on the row address and the column decoder 214 may specify a column of the memory rank based on the column address.

The CK receiver 221 may receive the clock signal CK from the memory controller 100. The CK receiver 221 may output the clock signal CK to the CMD/ADD receiver 210 and the synchronization circuit 220. The clock signal CK may provide a timing being a reference in overall operations of the memory device 200.

The WCK receiver 222 may receive the data clock signal WCK from the memory controller 100. The WCK receiver 222 may output the data clock signal WCK to the synchronization circuit 220.

The synchronization circuit 220 may receive the synchronization initiation signal SYI from the mode register 212. The synchronization circuit 220 may receive the clock signal CK from the CK receiver 221. The synchronization circuit 220 may receive the data clock signal WCK from the WCK receiver 222. The synchronization circuit 220 may perform synchronization of the data clock signal WCK based on the clock signal CK, in response to the synchronization initiation signal SYI. The synchronization circuit 220 may output a synchronized data clock signal SWCK to the internal clock circuit 223.

The synchronization of the data clock signal WCK may mean matching a timing with the clock signal CK and allowing the data clock signal WCK to toggle at a reference frequency, such that data are processed within the memory device 200. The reference frequency may be a frequency of the data clock signal WCK in a normal state, which is determined to read or write data in units of a bit. The reference frequency may be higher than a frequency of the clock signal CK. The synchronization of the data clock signal WCK will be described in more detail with reference to FIGS. 4A to 4C together.

The internal clock circuit 223 may receive the synchronized data clock signal SWCK from the synchronization circuit 220. The internal clock circuit 223 may output an internal clock signal to the I/O control circuit 230 based on the synchronized data clock signal SWCK. The internal clock signal may be used for the read operation and the write operation in the I/O control circuit 230. In an embodiment, the internal clock circuit 223 includes a four-phase converter. The four-phase converter will be described in more detail with reference to FIGS. 12A and 12B together.

The I/O control circuit 230 may be connected with the write data receiver 231, the read data transmitter 232, the internal clock circuit 223, and the plurality of memory ranks 240. The I/O control circuit 230 may be a circuit that controls the read operation and the write operation with the plurality of memory ranks 240. For example, the I/O control circuit 230 may receive data from the write data receiver 231. The I/O control circuit 230 may output data to the memory rank 240 through a write driver. For example, the I/O control circuit 230 may receive data from the memory rank 240 through a sense amplifier. The I/O control circuit 230 may output the data to the read data transmitter 232.

Each of the plurality of memory ranks 240 may be connected with the row decoder 213, the corresponding column decoder 214, and the corresponding write driver, and the corresponding sense amplifier. Each of the plurality of memory ranks 240 may include a plurality of memory banks. Each of the plurality of memory banks may include a plurality of memory cells. Each of the plurality of memory cells may have a row address and a column address and may store data in the form of logical high or logical low. How data are processed in the plurality of memory ranks 240 will be described in more detail with reference to FIGS. 10, 11A, and 11B together.

Figure 4A:
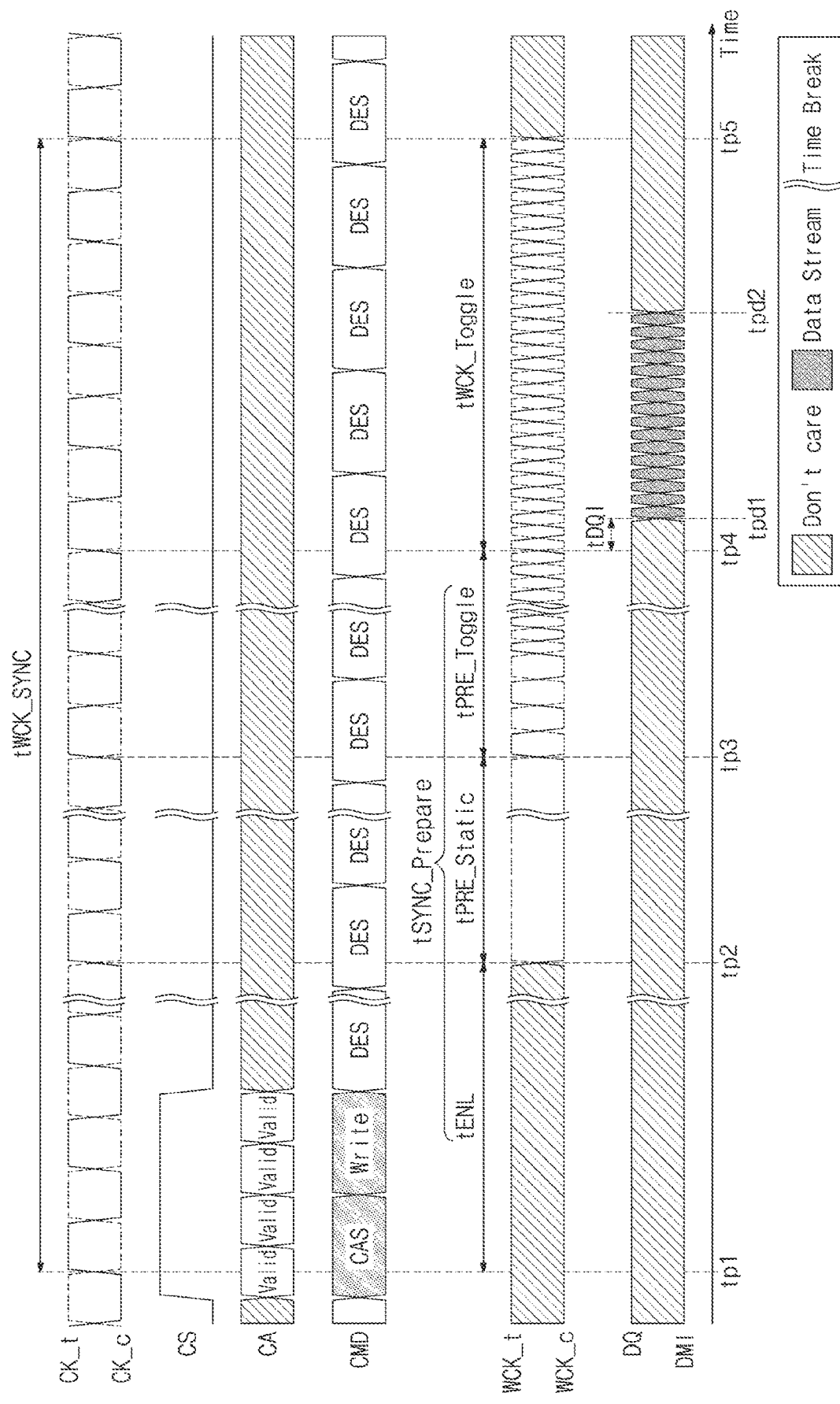
FIGS. 4A to 4C are timing diagrams illustrating synchronization of a data clock signal of FIG. 3, according to an embodiment of the present disclosure.
Figure 4B:
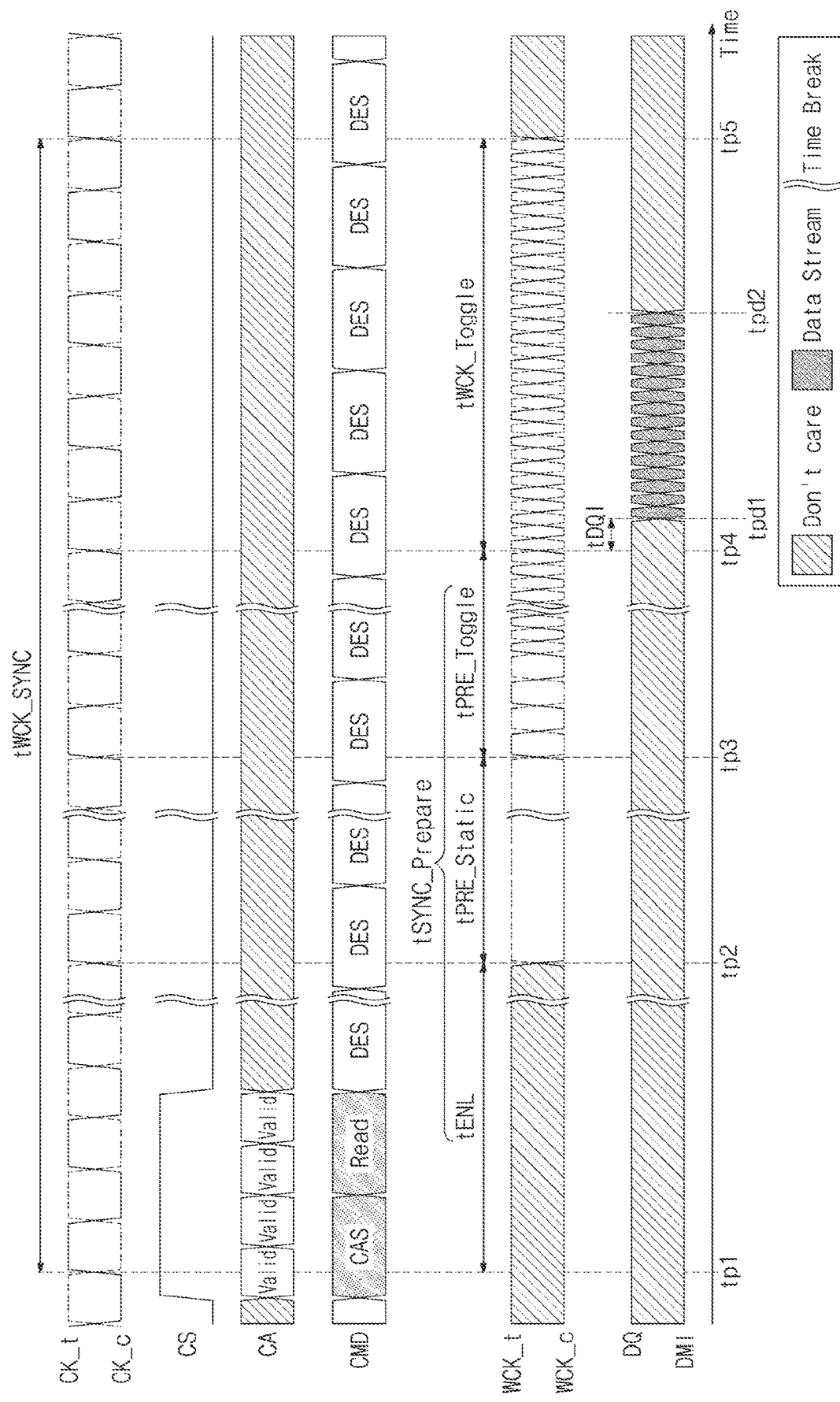
Figure 4C:
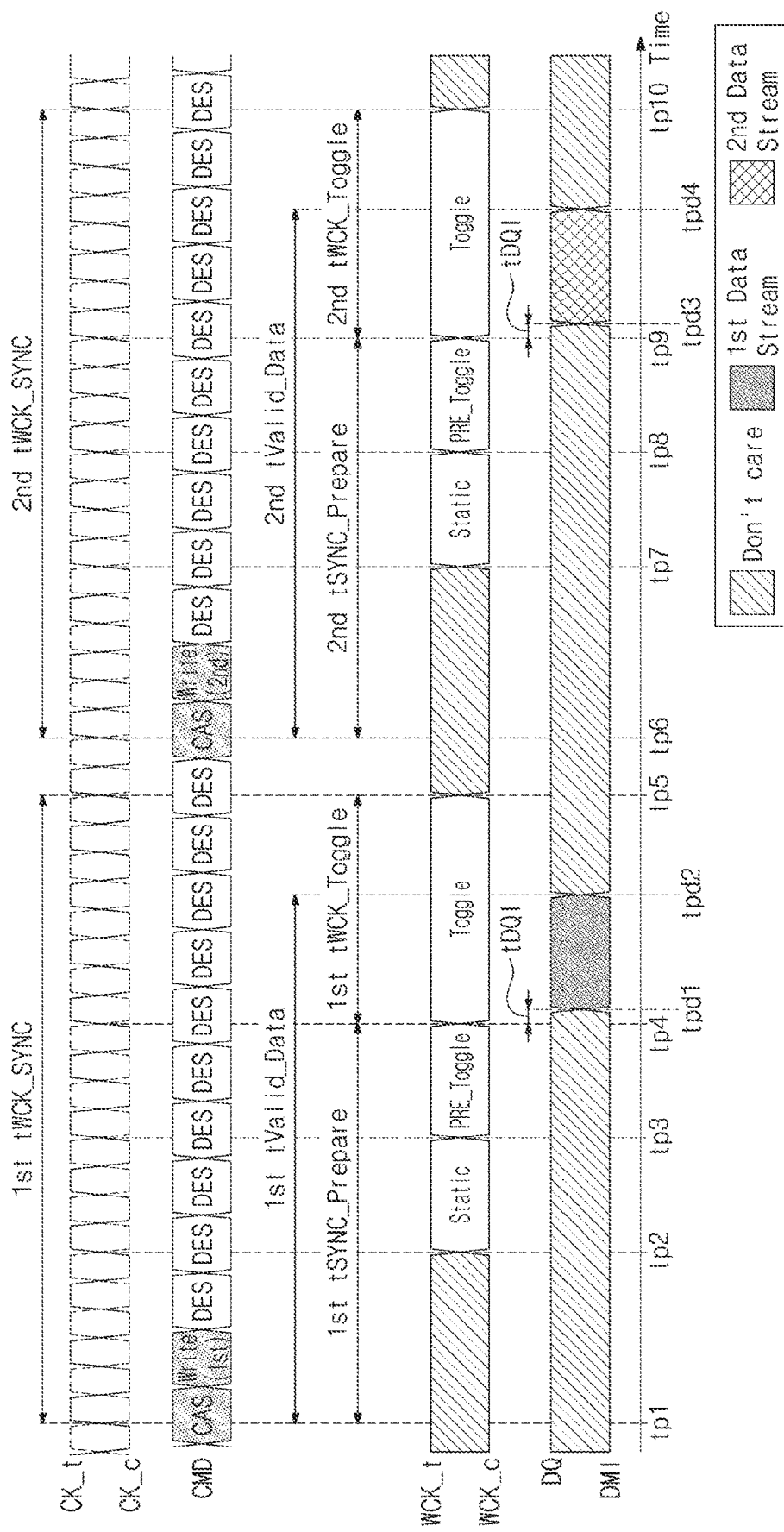

FIGS. 4A to 4C are timing diagrams illustrating synchronization of a data clock signal of FIG. 3, according to an embodiment of the present disclosure. For better understanding of the present invention, a case where the synchronization of a data clock signal is not extended will be described with reference to FIGS. 4A to 4C, and a case where the synchronization of the data clock signal is extended will be described with reference to FIGS. 5 to 16.

FIG. 4A describes a method for processing a data stream depending on the CAS and the write command. Referring to FIG. 4A, waveforms of CK_t, CK_c, CS, CA, CMD, WCK_t, WCK_c, DQ, and DMI are illustrated by way of example. In FIG. 4A, a horizontal axis represents a time. CK_t and CK_c may correspond to the clock CK of FIG. 3. A command/address signal CA may correspond to the command CMD and the address ADD of FIG. 3. A chip select signal CS may be a signal for activating the CA. The CMD may be determined based on a command truth table of the CA. WCK_t and WCK_c may correspond to the data clock signal WCK of FIG. 3. DQ and DMI may correspond to data of FIG. 3 (e.g., DQ and DMI for a write operation). To provide a better understanding of the present disclosure, the timing diagram of FIG. 4A will be described with reference to FIGS. 3 and 4A.

At time tp1, the memory device 200 detects toggling of the clock signal CK. For example, the memory device 200 may detect a transition of CK_t from logical low to logical high and/or a transition of CK_c from logical high to logical low. The memory device 200 may determine the CA in response to the toggling of the clock signal CK. The command CMD corresponding to the determined CA may be the CAS. At time tp1, WCK_t, WCK_c, DQ, and DMI may be in a don't care state.

The memory device 200 initiates the synchronization of the data clock signal WCK in response to the command CMD being determined as the CAS. For example, time tp1 may be a start point of a time period tWCK_SYNC indicating a period associated with the synchronization of the data clock signal WCK. For example, time tp1 may be a start point of a preparation time period tSYNC_Prepare indicating a period of preparing the synchronization of the data clock signal WCK.

In an embodiment, immediately after receiving the CAS, the memory device 200 may receive the command CMD corresponding to a write. For example, the memory device 200 may sequentially receive the CAS and the command CMD corresponding to the write. In an embodiment, a time period from when a command corresponding to the write is applied to when the data DQ and DMI are processed may be determined in advance depending on the specification applied to the memory device 200.

At time tp2, the memory device 200 determines that a time period tENL passes from time tp1 when the CAS is determined. The time period tENL may indicate a period where the data clock signal WCK is in the don't care state. The memory device 200 may maintain the data clock signal WCK in a given logical state from time tp2. For example, the memory device 200 may maintain WCK_t at logical low and may maintain WCK_c at logical high.

At time tp3, the memory device 200 determines that a time period tPRE_Static passes from time tp2 when the data clock signal WCK is maintained in the given logical state. The time period tPRE_Static may indicate a period where the data clock signal WCK is maintained in the given logical state. The memory device 200 may perform pre-toggling of the data clock signal WCK after time tp3. The pre-toggling may mean that the data clock signal WCK toggles at a frequency lower than the reference frequency. For example, the memory device 200 may allow the data clock signal WCK to toggle at a frequency, which is lower than the reference frequency as much as two times, during a time period tPRE_Toggle from time tp3. However, the present disclosure is not limited thereto. For example, according to an embodiment, the memory device 200 allows the data clock signal WCK to toggle at the reference frequency in the time period tPRE_Toggle.

At time tp4, the memory device 200 determines that the time period tPRE_Toggle passes from time tp3 when the data clock signal WCK pre-toggles at a frequency lower than the reference frequency. The time period tPRE_Toggle may indicate a period where the data clock signal WCK pre-toggles at the frequency lower than the reference frequency. In an embodiment, the memory device 200 allows the data clock signal WCK to toggle at the reference frequency after time tp4. The reference frequency that is a frequency used to read or write data in units of a bit may be a frequency of the data clock signal WCK in a normal state. For example, the reference frequency may correspond to a frequency of the DQ.

At time tpd1, the memory device 200 may initiate processing of a data stream. The data stream may indicate a set of DQs corresponding to valid data. For example, the memory device 200 may store the DQ based on the data clock signal WCK from time tpd1.

In an embodiment, the memory device 200 processes a data stream from time tpd1 when a time period tDQI passes from time tp4. The time period tDQI may be a margin that is set to cope with an abnormal operation (e.g., the situation where a frequency of the data clock signal WCK does not yet converge to the reference frequency). In an embodiment, the time period tDQI is omitted or may be decreased or increased.

At time tpd2, the memory device 200 completes the processing of the data stream. The data clock signal WCK that toggles after time tpd2 may be irrelevant to the processing of the data stream. In the case where processing of another data stream is not required, the toggling of the data clock signal WCK after time tpd2 may cause unnecessary power consumption. At time tp5, the memory device 200 may disable the synchronization of the data clock signal WCK. To disable the synchronization may mean that the data clock signal WCK does not toggle or that the data clock signal WCK is in the don't care state without solving a skew with the clock signal CK. After time tp5, since the synchronization of the data clock signal WCK is disabled, power consumption of the memory device 200 may be reduced. In the case of a mobile device in which a power supply is limited, disabling the synchronization of the data clock signal WCK when data processing is not required may be useful for power management.

In an embodiments, time tp5 when the synchronization of the data clock signal WCK is disabled may be determined as a time when a time period tWCK_Toggle passes from time tp4 when the data clock signal WCK toggles. The time period tWCK_Toggle may comply with settings in the mode register 212 of the memory device 200. Time tp5 may be an end point of the time period tWCK_SYNC.

As described above, the synchronization of the data clock signal WCK corresponding to the CAS and the write command is described with reference to FIG. 4A. The time period tWCK_SYNC associated with the synchronization of the data clock signal WCK may be a time period from tp1 to tp5. The time period tWCK_SYNC may include the preparation time period tSYNC_Prepare and the time period tWCK_Toggle. The preparation time period tSYNC_Prepare may include the time period tENL, the time period tPRE_Static, and the time period tPRE_Toggle. The time period tWCK_Toggle may indicate a period where the data clock signal WCK toggles at the reference frequency. After the time period tDQI passes from time tp4 being a start point of the time period tWCK_Toggle, a data stream may be processed.

FIG. 4B describes a method for processing a data stream depending the CAS and the read command. Referring to FIG. 4B, waveforms of CK_t, CK_c, CS, CA, CMD, WCK_t, WCK_c, DQ, and DMI are illustrated by way of example. In FIG. 4B, a horizontal axis represents a time. In each waveform, the meaning and a correspondence relationship of the memory device 200 are similar to those described with reference to FIG. 4A, and thus, additional description will be omitted to avoid redundancy. The timing diagram of FIG. 4B will be described with reference to FIGS. 3 and 4B.

Even in the case of processing the read command as well as the write command, the memory device 200 may process data based on the synchronization of the data clock signal WCK. For example, the memory device 200 may prepare the toggling of the data clock signal WCK during the preparation time period tSYNC_Prepare and may then process a data stream within the time period tWCK_Toggle.

In more detail, based on the CAS and the read command sequentially received, the memory device 200 may maintain the data clock signal WCK in the don't care state during the time period tENL, may maintain the data clock signal WCK in the given logical state during the time period tPRE_Static, and may perform pre-toggling of the data clock signal WCK at a frequency lower than the reference frequency during the time period tPRE_Toggle. After the time period tDQI for margin passes from time tp4 being a start point of the time period tWCK_Toggle, the memory device 200 may output the data stream depending on the read command.

As described above, the method for processing the data stream in the write operation is described with reference to FIG. 4A, and the method for processing the data stream in the read operation is described with reference to FIG. 4B. After the data stream is processed, the synchronization of the data clock signal WCK may be disabled, and thus, power consumption of the memory device 200 may be reduced. However, after the synchronization of the data clock WCK signal is disabled, when another read command or a write command is received, the memory device 200 may again perform the synchronization of the data clock signal WCK. This will be more fully described with reference to FIG. 4C together.

FIG. 4C describes a method for processing a plurality of data streams. Referring to FIG. 4C, waveforms of CK_t, CK_c, CMD, WCK_t, WCK_c, DQ, and DMI are illustrated by way of example. In FIG. 4C, a horizontal axis represents a time. In each waveform, the meaning and a correspondence relationship of the memory device 200 are similar to those described with reference to FIG. 4A, and thus, additional description will be omitted to avoid redundancy. The timing diagram of FIG. 4C will be described with reference to FIGS. 3 and 4C.

The memory device 200 may process a plurality of data streams. For example, the memory device 200 may process a first data stream during a time period 1st tWCK_SYNC. Afterwards, the memory device 200 may process a second data stream during a time period 2nd tWCK_SYNC.

The time period 1st tWCK_SYNC may be a time period from tp1 to tp5. Time tp1 may be a time at which the CAS corresponding to a first write command is determined. Time tp5 may be a time at which the toggling of the data clock signal WCK for a first write operation ends. The time period 1st tWCK_SYNC may include a time period 1st tValid_Data. The time period 1st tValid_Data may be a time period from time tp1 when a command associated with the first data stream is determined to time tpd2 when processing of the first data stream is completed.

The time period 1st tWCK_SYNC may include a preparation time period 1st tSYNC_Prepare and a time period 1st tWCK_Toggle. The preparation time period 1st tSYNC_Prepare may be a time period from time tp1 when the command associated with the first data stream is determined to time tp4 when the data clock signal WCK toggles at the reference frequency. The preparation time period 1st tSYNC_Prepare may include a time period in which the data clock signal WCK is in the don't care state, a time period in which the data clock signal WCK is maintained in the given logical state, and a time period in which the data clock signal WCK pre-toggles at a frequency lower than the reference frequency.

The time period 1st tWCK_Toggle may be a time period from time tp4 when the data clock signal WCK toggles at the reference frequency to time tp5 when the synchronization of the data clock signal WCK is disabled. In the time period 1st tWCK_Toggle, the memory device 200 may start to process the first data stream from time tpd1 when the time period tDQI passes from time tp4. At time tpd2, the memory device 200 may complete the processing of the first data stream.

The time period 2nd tWCK_SYNC may be a time period from tp6 to tp10. Time tp6 may be a time at which the CAS corresponding to a second write command is determined. Time tp10 may be a time at which the toggling of the data clock signal WCK for a second write operation ends. The time period 2nd tWCK_SYNC may include a time period 2nd tValid_Data. The time period 2nd tValid_Data may be a time period from time tp6 when a command associated with the second data stream is determined to time tpd4 when processing of the second data stream is completed.

The time period 2nd tWCK_SYNC may include a preparation time period 2nd tSYNC_Prepare and a time period 2nd tWCK_Toggle. The preparation time period 2nd tSYNC_Prepare may be a time period from time tp6 when the command associated with the second data stream is determined to time tp9 when the data clock signal WCK toggles at the reference frequency. The preparation time period 2nd tSYNC_Prepare may include a time period in which the data clock signal WCK is in the don't care state, a time period in which the data clock signal WCK is maintained in the given logical state, and a time period in which the data clock signal WCK pre-toggles at a frequency lower than the reference frequency.

The time period 2nd tWCK_Toggle may be a time period from time tp9 when the data clock signal WCK toggles at the reference frequency to time tp10 when the synchronization of the data clock signal WCK is disabled. In the time period 2nd tWCK_Toggle, the memory device 200 may start to process the second data stream from time tpd3 when the time period tDQI passes from time tp9. At time tpd4, the memory device 200 may complete the processing of the second data stream.

As described above, in the memory device 200, the synchronization of the data clock signal WCK may be disabled to reduce power consumption after data processing is completed. However, in the case where a new write command or a new read command is received later, the memory device 200 again performs the synchronization of the data clock signal WCK, thereby causing a delay of data processing. Accordingly, there is required a method for extending the synchronization of the data clock signal WCK in the memory device 200. This will be more fully described with reference to FIGS. 5 to 9 together.

Figure 5:
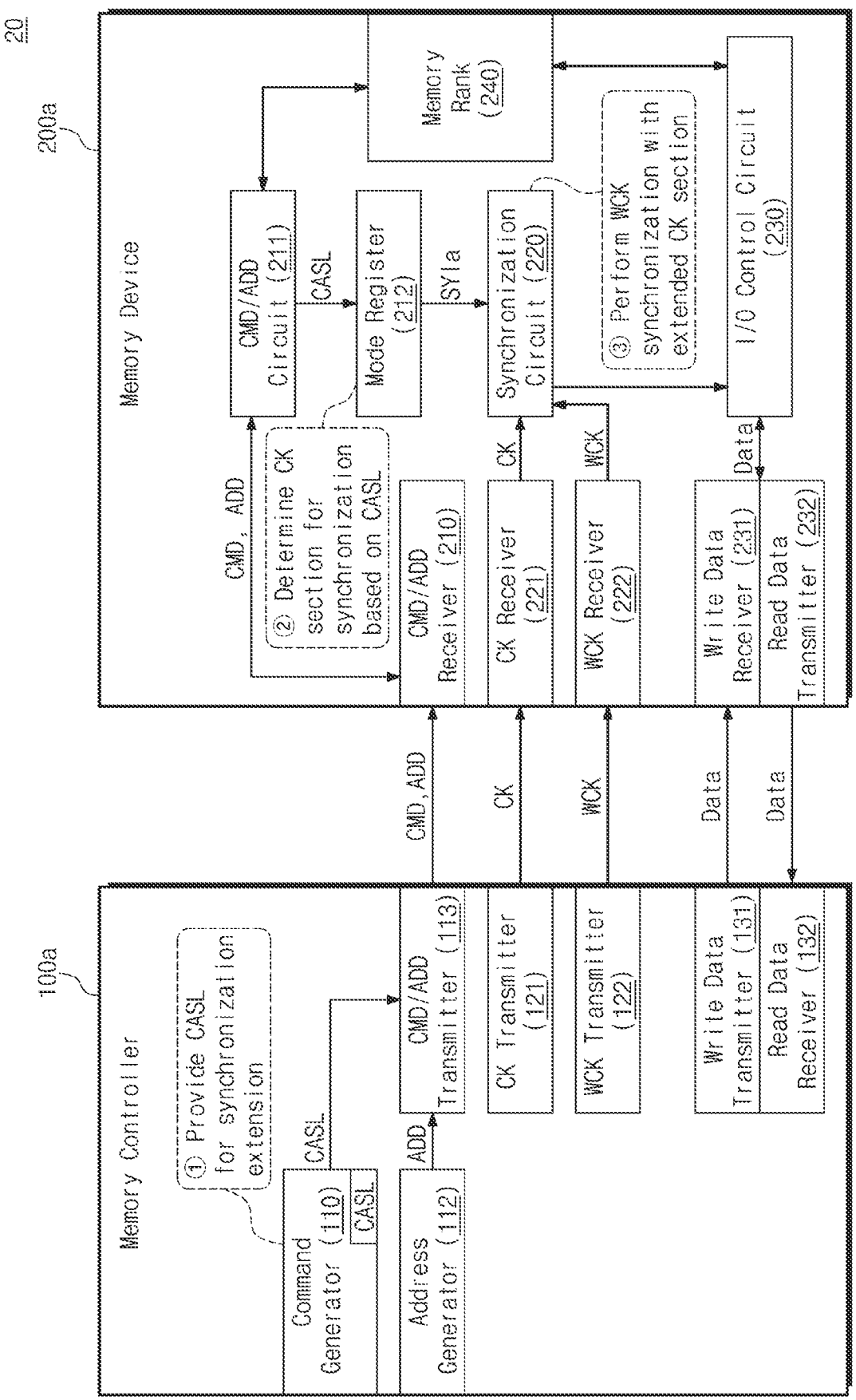
FIG. 5 is a block diagram illustrating an electronic device according to an embodiment of the present disclosure.

FIG. 5 is a block diagram illustrating an electronic device according to an embodiment of the present disclosure. Referring to FIG. 5, an electronic device 20 includes a memory controller 100a and a memory device 200a. The memory controller 100a includes the command generator 110, the address generator 112, the CMD/ADD transmitter 113, the CK transmitter 121, the WCK transmitter 122, the write data transmitter 131, and the read data receiver 132. The memory device 200a includes the CMD/ADD receiver 210, the CMD/ADD circuit 211, the mode register 212, the synchronization circuit 220, the CK receiver 221, the WCK receiver 222, the I/O control circuit 230, the write data receiver 231, the read data transmitter 232, and the memory rank 240. Lower level components of the electronic device 20 are similar to those described with reference to FIGS. 1 to 3, and thus, additional description will be omitted to avoid redundancy.

According to an embodiment of the present disclosure, the electronic device 20 extends the synchronization of the data clock signal WCK based on the CASL defined by the user. The CASL may be a command defined by the user. The CASL may define a clock section that indicates initiation of the synchronization of the data clock signal WCK and corresponds to the synchronization. In an embodiment, the clock section defined in the CASL is longer than a clock section defined in the CAS of the LPDDR5.

According to an embodiment of the present disclosure, the command generator 110 may include the CASL being the defined command. The CASL may be provided from the host. To extend the synchronization, the command generator 110 may output the CASL to the CMD/ADD transmitter 113. The CMD/ADD transmitter 113 may output the CASL to the CMD/ADD receiver 210 in the form of the command CMD. The CMD/ADD receiver 210 may output the command CMD including the CASL to the CMD/ADD circuit 211. The CMD/ADD circuit 211 may decode the command CMD to obtain the CASL. The CMD/ADD circuit 211 may output the CASL to the mode register 212.

The mode register 212 may receive the CASL from the CMD/ADD circuit 211. The mode register 212 may determine the clock section for the synchronization, based on the CASL. In this case, the determined clock section may be longer than the clock section corresponding to the CAS. The mode register 212 may output a synchronization initiation signal SYIa to the synchronization circuit 220. For example, the mode register 212 may output the synchronization initiation signal SYIa in response to receiving the CASL. The synchronization initiation signal SYIa may include information about the clock section according to the CASL.

The synchronization circuit 220 may receive the synchronization initiation signal SYIa from the mode register 212. The synchronization circuit 220 may perform the synchronization of the data clock signal WCK during an extended clock section, based on the synchronization initiation signal SYIa.

Figure 6:
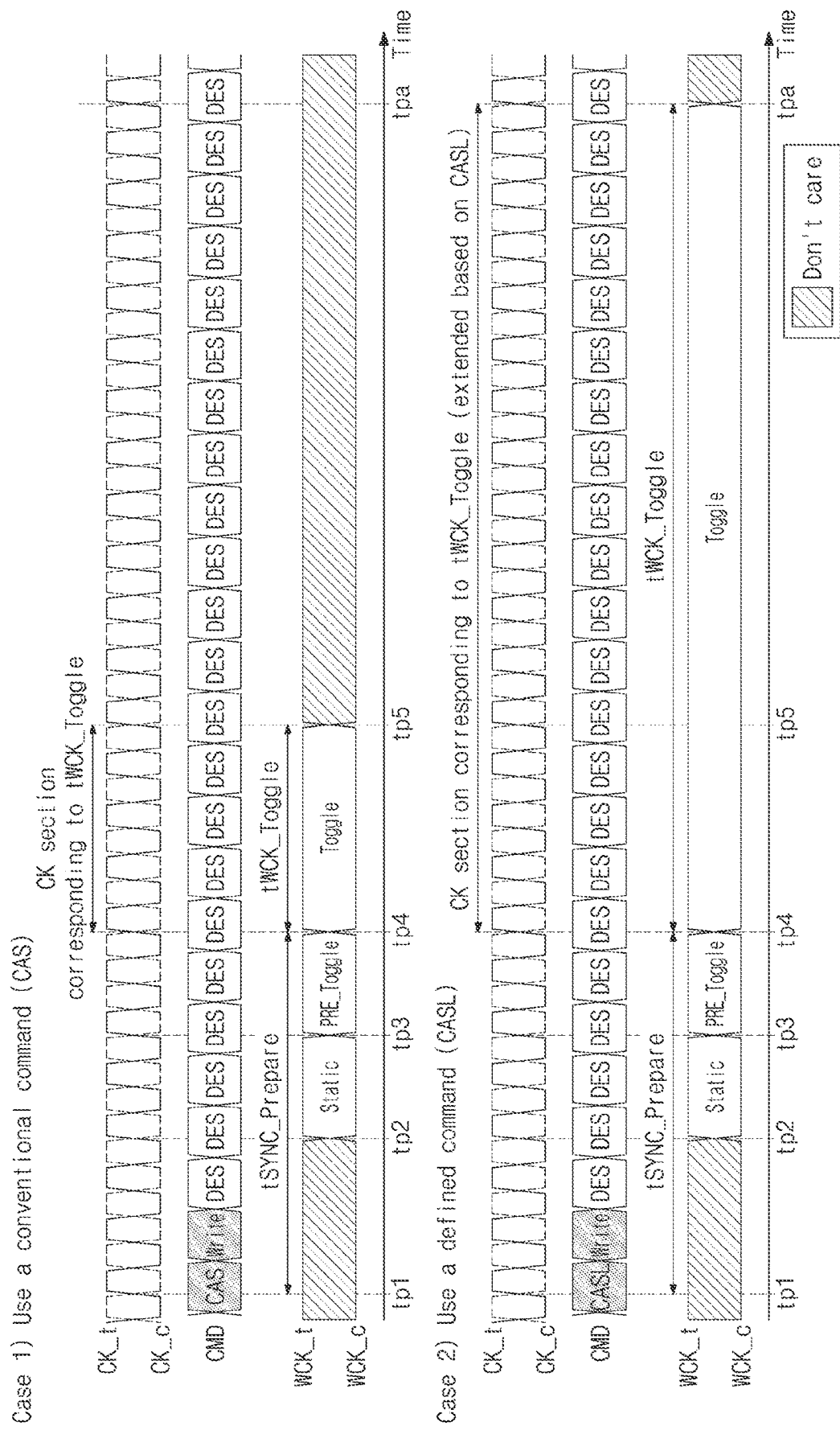
FIG. 6 is a timing diagram illustrating a data clock signal in which the synchronization in FIG. 5 is extended, according to an embodiment of the present disclosure.

FIG. 6 is a timing diagram illustrating a data clock signal in which the synchronization in FIG. 5 is extended, according to an embodiment of the present disclosure. A timing diagram indicating synchronization in the case of using the CAS and a timing diagram indicating synchronization in the case of using the CASL are illustrated in FIG. 6. For example, the case of using the CAS may correspond to the memory device 200 of FIG. 1, and the case of using the CASL may correspond to the memory device 200a of FIG. 5. In FIG. 6, a horizontal axis represents a time. In each waveform, the meaning and a correspondence relationship of the memory device are similar to those described with reference to FIG. 4A, and thus, additional description will be omitted to avoid redundancy.

Referring to FIG. 6 associated with the case of using the CAS and FIG. 1, in response to that the command CMD is determined as the CAS, the memory device 200 may prepare the toggling of the data clock signal WCK during the preparation time period tSYNC_Prepare and may allow the data clock signal WCK to toggle during the time period tWCK_Toggle. In this case, the time period tWCK_Toggle may correspond to a clock section.

Referring to FIG. 6 associated with the case of using the CASL and FIG. 5, in response to the command CMD being determined as the CASL, the memory device 200a prepares the toggling of the data clock signal WCK during the preparation time period tSYNC_Prepare and allows the data clock signal WCK to toggle during the time period tWCK_Toggle. In this case, the time period tWCK_Toggle corresponds to the clock section defined in the CASL.

That is, in the case of using the CAS, the clock section corresponding to the time period tWCK_Toggle may be from tp4 to tp5. In the case of using the CASL, the clock section corresponding to the time period tWCK_Toggle may be from tp4 to tpa. As the clock section corresponding to the time period tWCK_Toggle is extended based on the defined CASL, the time period tWCK_Toggle may be extended as much as a time period from tp5 to tpa.

Figure 7:
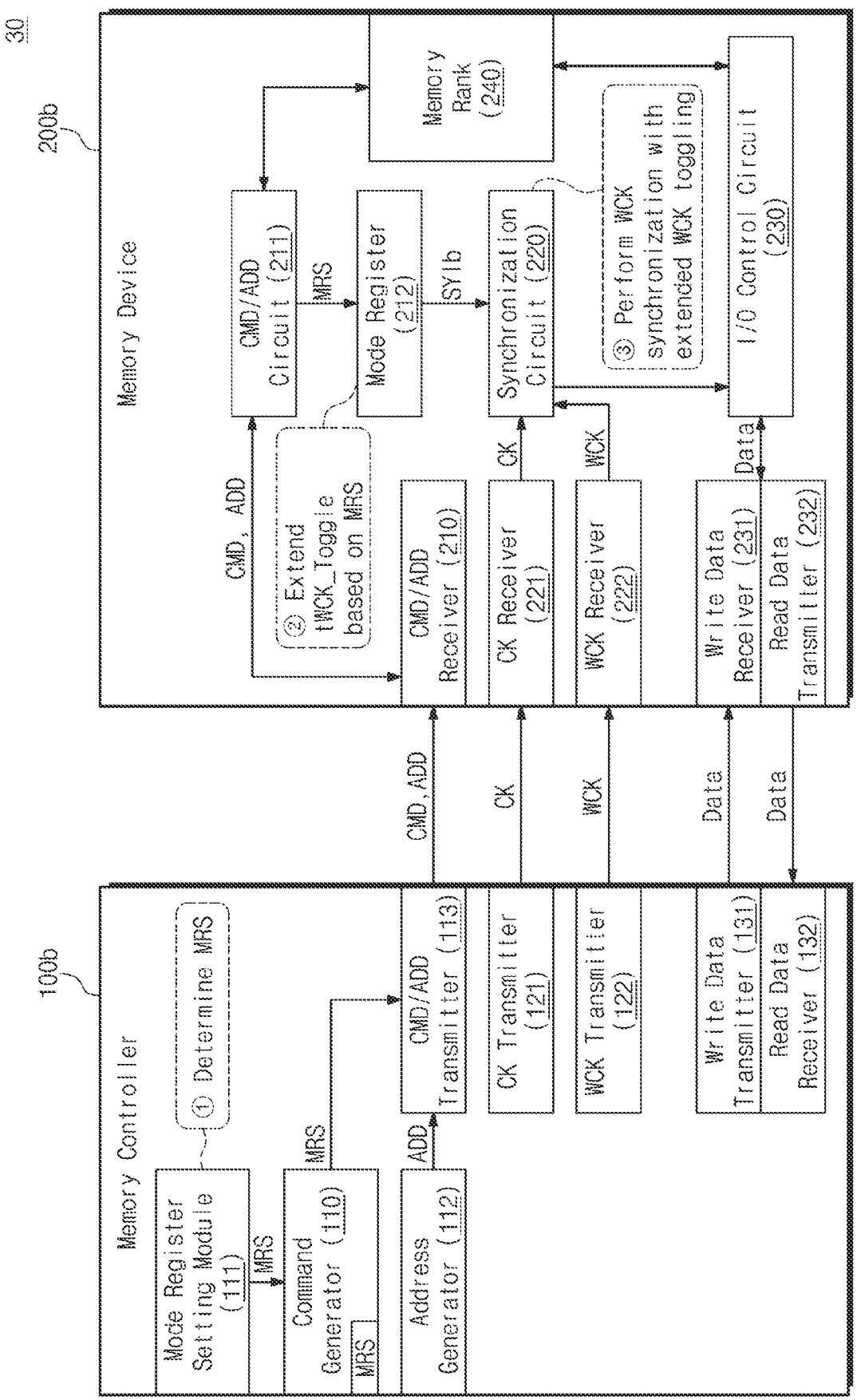
FIG. 7 is a block diagram illustrating an electronic device according to an embodiment of the present disclosure.

FIG. 7 is a block diagram illustrating an electronic device according to an embodiment of the present disclosure. Referring to FIG. 7, an electronic device 30 includes a memory controller 100b and a memory device 200b. The memory controller 100b includes the command generator 110, the mode register setting module 111, the address generator 112, the CMD/ADD transmitter 113, the CK transmitter 121, the WCK transmitter 122, the write data transmitter 131, and the read data receiver 132. The memory device 200b includes the CMD/ADD receiver 210, the CMD/ADD circuit 211, the mode register 212, the synchronization circuit 220, the CK receiver 221, the WCK receiver 222, the I/O control circuit 230, the write data receiver 231, the read data transmitter 232, and the memory rank 240. Lower level components of the electronic device 30 are similar to those described with reference to FIGS. 1 to 3, and thus, additional description will be omitted to avoid redundancy.

According to an embodiment of the present disclosure, the electronic device 30 may extend the synchronization of the data clock signal WCK by changing settings of the mode register 212, based on a command including the mode register setting information MRS. The mode register setting information MRS may be set by the user. In an embodiment, the mode register setting information MRS include a reference cycle count (or number) of the data clock signal WCK.

The reference cycle count (or number) may indicate the number of times that the data clock signal WCK toggles in the synchronization of the data clock signal WCK. For example, the reference cycle count (or number) that is the number of times defined by the user may be greater than the number of times that the data clock signal WCK toggles, which is defined in the mode register 212.

According to an embodiment of the present disclosure, the mode register setting module 111 may determine the mode register setting information MRS. Alternatively, the mode register setting information MRS may be received from the host. The mode register setting module 111 may output the mode register setting information MRS to the command generator 110. The command generator 110 may output the mode register setting information MRS to the CMD/ADD transmitter 113. The CMD/ADD transmitter 113 may output the command CMD including the mode register setting information MRS to the CMD/ADD receiver 210. The CMD/ADD receiver 210 may output the command CMD including the mode register setting information MRS to the CMD/ADD circuit 211. The CMD/ADD circuit 211 may decode the command CMD to obtain the mode register setting information MRS. The CMD/ADD circuit 211 may output the mode register setting information MRS to the mode register 212.

Settings of the mode register 212 may be changed based on the mode register setting information MRS. For example, based on the mode register setting information MRS, the mode register 212 may determine the number of times that the data clock signal WCK toggles in the time period tWCK_Toggle, as the reference cycle count (or number). In an embodiment, the reference cycle count (or number) is greater than the number of times that the data clock signal WCK toggles in the time period tWCK_Toggle. The mode register 212 may output a synchronization initiation signal SYIb to the synchronization circuit 220. For example, the mode register 212 may output a synchronization initiation signal SYIb in response to receiving the mode register setting information MRS.

The synchronization circuit 220 may receive the synchronization initiation signal SYIb from the mode register 212. The synchronization circuit 220 may extend the synchronization of the data clock signal WCK, based on the synchronization initiation signal SYIb.

Figure 8:
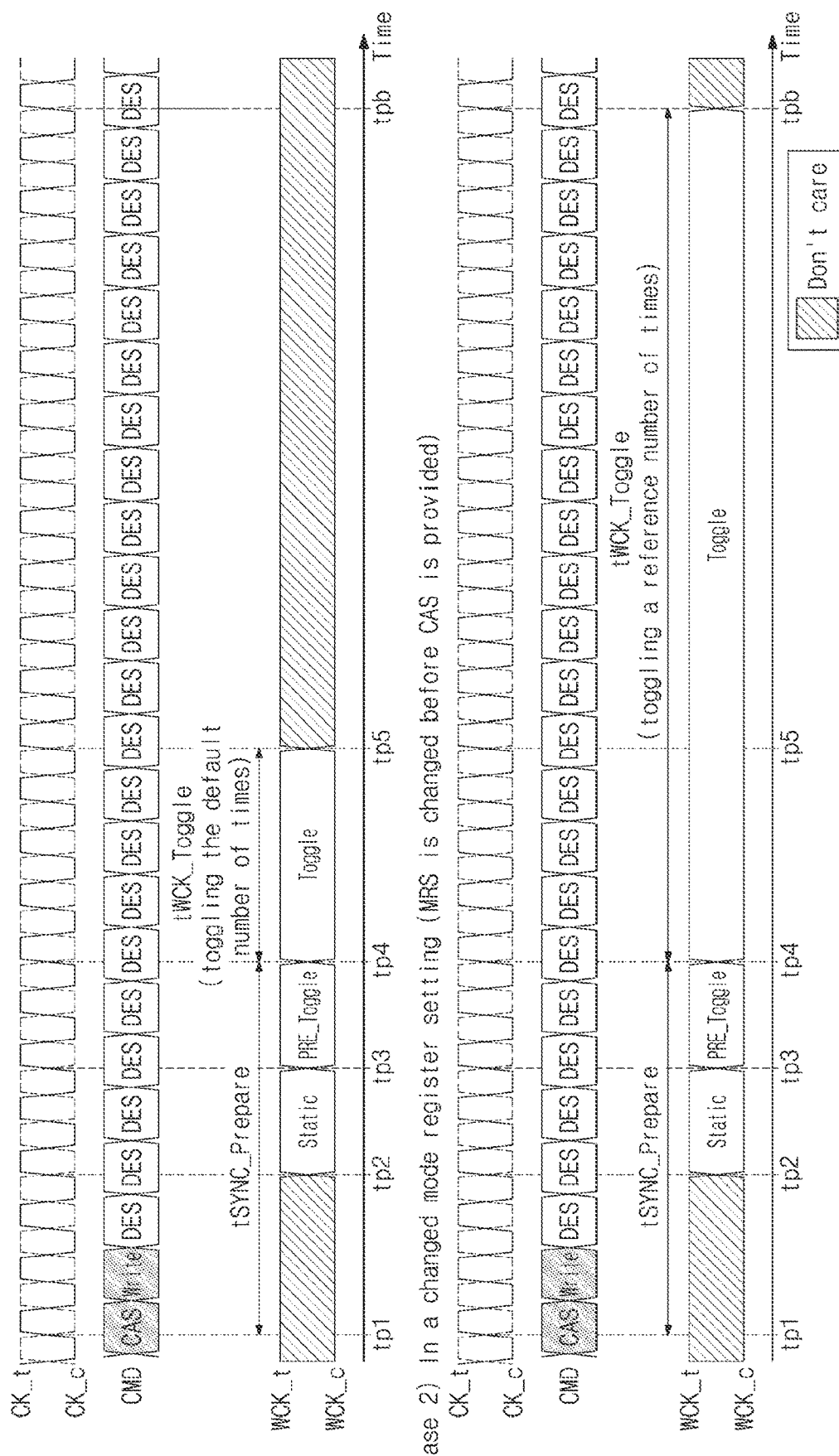
FIG. 8 is a timing diagram illustrating a data clock signal in which the synchronization in FIG. 7 is extended, according to an embodiment of the present disclosure.

FIG. 8 is a timing diagram illustrating a data clock signal in which the synchronization in FIG. 7 is extended, according to an embodiment of the present disclosure. A timing diagram indicating synchronization performed depending on conventional mode register setting and a timing diagram indicating synchronization performed depending on changed mode register setting are illustrated in FIG. 8. For example, the case of the conventional mode register setting may correspond to the memory device 200 of FIG. 1, and the case of the changed mode register setting may correspond to the memory device 200b of FIG. 7. In FIG. 8, a horizontal axis represents a time. In each waveform, the meaning and a correspondence relationship of the memory device are similar to those described with reference to FIG. 4A, and thus, additional description will be omitted to avoid redundancy.

Referring to FIG. 8 associated with the conventional mode register setting and FIG. 1, in response to that the command CMD is determined as the CAS, the memory device 200 may prepare the toggling of the data clock signal WCK during the preparation time period tSYNC_Prepare and may allow the data clock signal WCK to toggle during the time period tWCK_Toggle. The number of times that the data clock signal WCK toggles in the time period tWCK_Toggle may comply with a setting in the mode register 212. For example, during the time period tWCK_Toggle, the data clock signal WCK may toggle by as much as a default cycle count (or number).

Referring to FIG. 8 associated with the changed mode register setting and FIG. 7, the memory device 200b may receive the mode register setting information MRS before time tp1. The mode register 212 of the memory device 200b may change settings based on the mode register setting information MRS. For example, with regard to the synchronization of the data clock signal WCK, the mode register 212 may determine the number of times that the data clock signal WCK toggles in the time period tWCK_Toggle, as the reference cycle count (or number) instead of the default cycle count (or number). At time tp1, in response to the command CMD being determined as the CASL, the memory device 200b may prepare the toggling of the data clock signal WCK during the preparation time period tSYNC_Prepare and may allow the data clock signal WCK to toggle during the time period tWCK_Toggle. In this case, the number of times that the data clock signal WCK toggles in the time period tWCK_Toggle may comply with the changed setting in the mode register 212. For example, during the time period tWCK_Toggle, the data clock signal WCK may toggle by as much as the reference cycle count (or number). In an embodiment, the reference cycle count (or number) is greater than the default cycle count (or number).

That is, a frequency of the data clock signal WCK may be uniform during the time period tWCK_Toggle, and the time period tWCK_Toggle that is based on the data clock signal WCK toggling by as much as the default cycle number may be from tp4 to tp5. The time period tWCK_Toggle that is based on the data clock signal WCK toggling by as much as the reference cycle number may be from tp4 to tpb. As the number of times that the data clock signal WCK toggles increases during the time period tWCK_Toggle, the time period tWCK_Toggle may be extended by as much as a time period from tp5 to tpb.

Figure 9:
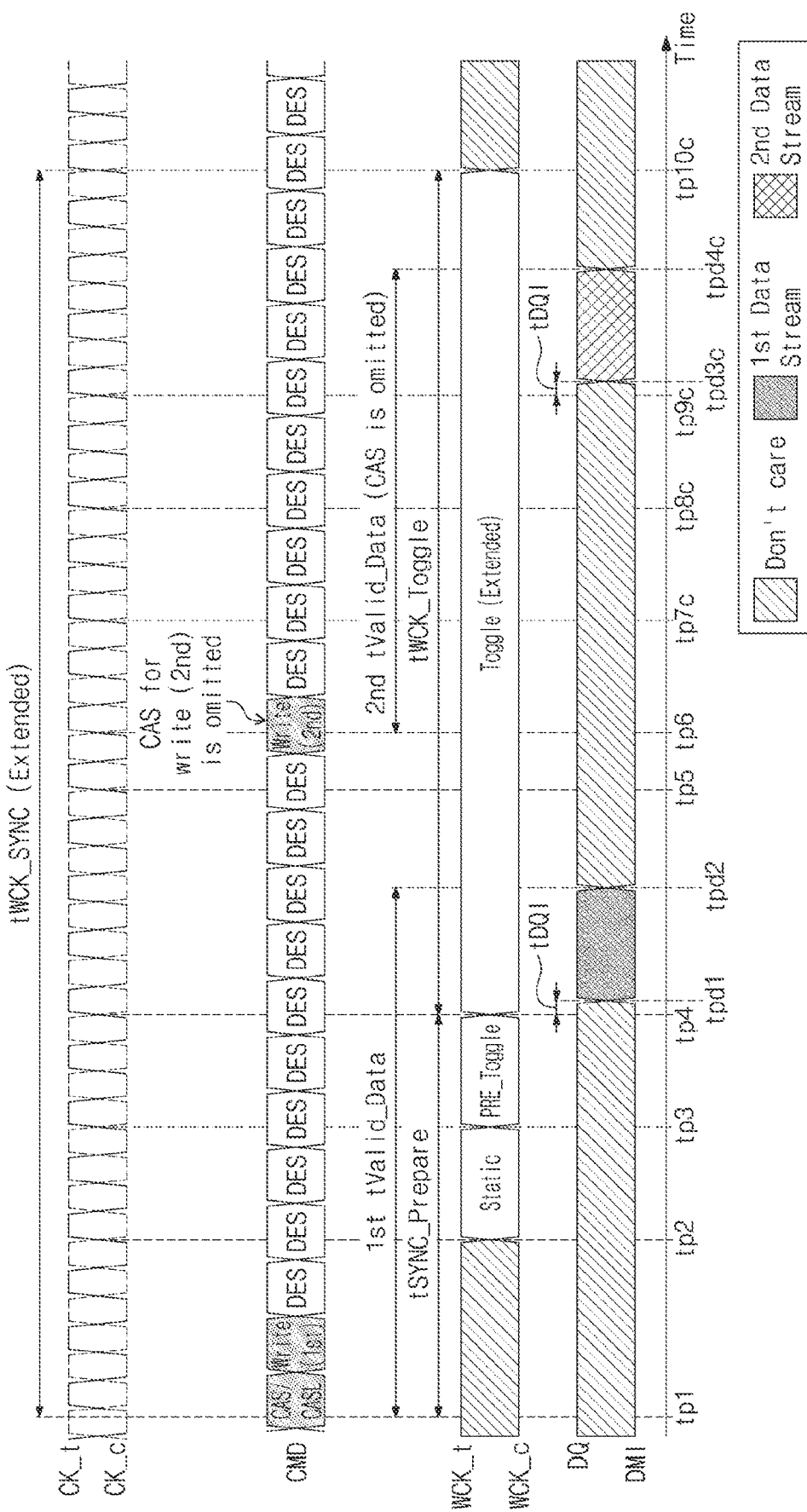
FIG. 9 is a timing diagram illustrating data streams that are processed based on a data clock signal in which synchronization is extended, according to an embodiment of the present disclosure.

FIG. 9 is a timing diagram illustrating data streams that are processed based on a data clock signal in which synchronization is extended, according to an embodiment of the present disclosure. A method for processing a plurality of data streams based on the extended data clock signal WCK will be described with reference to FIG. 9. In each waveform, the meaning and a correspondence relationship of the memory device are similar to those described with reference to FIG. 4A, and thus, additional description will be omitted to avoid redundancy. The timing diagram of FIG. 9 may correspond to the synchronization in the memory device 200a of FIG. 5 or the synchronization in the memory device 200b of FIG. 7.

In an embodiment, at time tp1, a command may be determined as the CASL. In an embodiment, the command CMD for changing settings of a mode register before time tp1 is received, and the number of times that the data clock signal WCK toggles is determined as the reference cycle count (or number). At time tp1, a command may be determined as the CAS.

During the preparation time period tSYNC_Prepare from time tp1, a memory device prepares toggling of the data clock signal WCK. During the time period tWCK_Toggle from time tp4, the memory device allows the data clock signal WCK to toggle. In this case, the time period tWCK_Toggle may be a time period extended based on the CASL or the setting change of the mode register. For example, the time period tWCK_Toggle may be longer than the first time period 1st tWCK_Toggle of FIG. 4C. In an embodiment, the first time period 1st tWCK_Toggle has a first duration and the duration of the time period tWCK_Toggle is a sum of the first duration and a second duration of the clock section indicated by the CASL or the setting change. Thus, the duration of the time period tWCK_Toggle is extended by the second duration.

At time tp5, the data clock signal WCK may continuously toggle. Because the synchronization of the data clock signal WCK is not disabled, a command for initiation of the synchronization may not be required. For example, because the toggling of the data clock signal WCK is maintained at time tp5, the CAS for a second write operation may not be required. Since one cycle where the command CMD for the CAS is received is omitted, the time period 2nd tValid_Data may be shortened. As such, processing of the second data stream may quicken. For example, a time tpd4c when the processing of the second data stream is completed may be earlier than a time tpd4 of FIG. 4C, at which the processing of the second data stream is completed.

In an embodiment, a command received immediately before the second write command is not the CAS command in the LPDDR5. For example, the CA received at time tp6 may be determined as a write command based on the command truth table, and the CA received at time tp5 may be determined as the DES (i.e., as not being the CAS) based on the command truth table.

As described above, according to an embodiment of the present disclosure, there is provided a method for improving a speed, at which data are processed in a memory device, by extending the synchronization of the data clock signal WCK.

Figure 10:
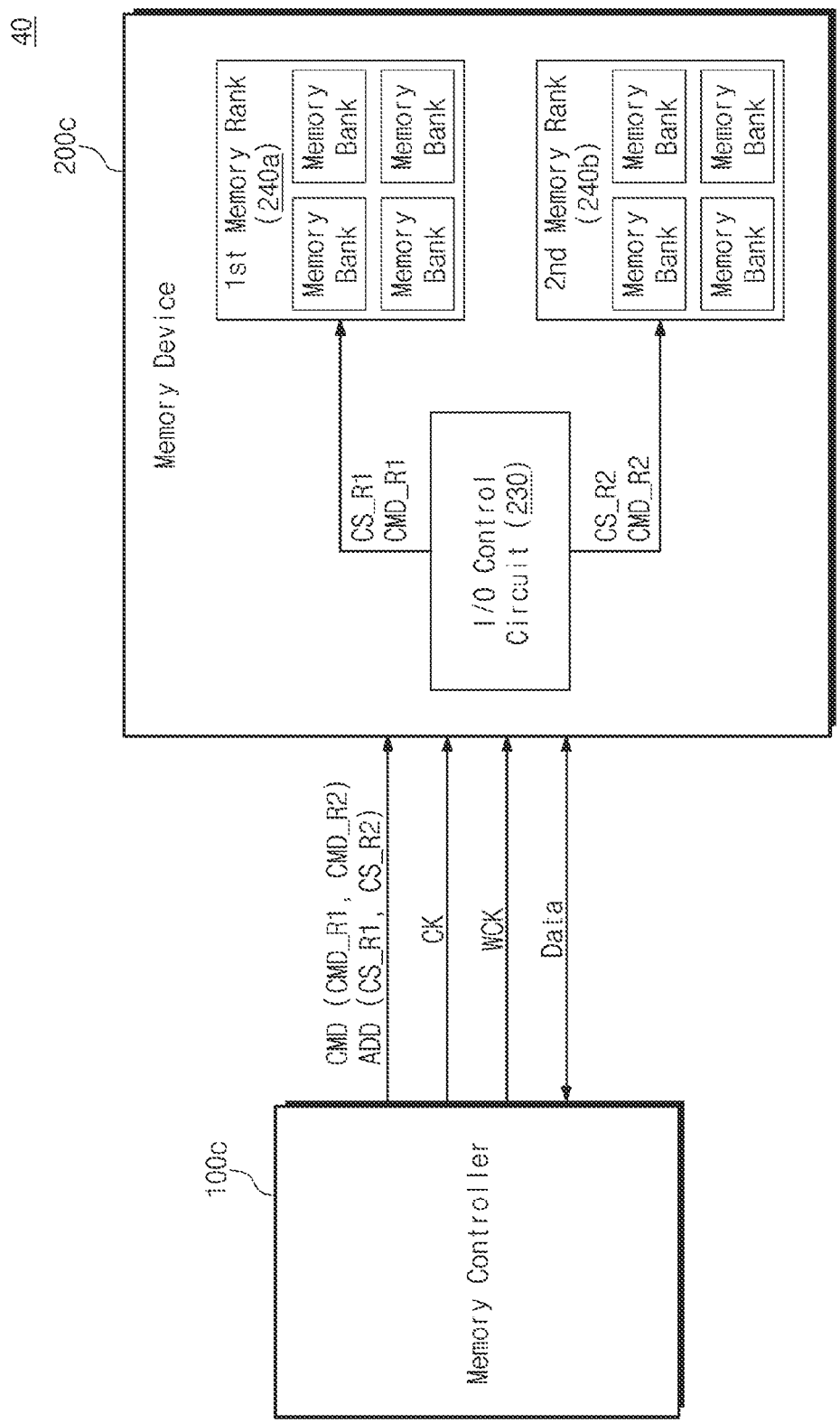
FIG. 10 is a block diagram illustrating an electronic device according to an embodiment of the present disclosure.

FIG. 10 is a block diagram illustrating an electronic device according to an embodiment of the present disclosure. Referring to FIG. 10, an electronic device 40 includes a memory controller 100c and a memory device 200c. The memory device 200c includes the I/O control circuit 230, a first memory rank 240a, and a second memory rank 240b. Each of the first memory rank 240a and the second memory rank 240b may include a plurality of memory banks. The memory controller 100c may output the command CMD, the address ADD, the clock signal CK, and the data clock signal WCK to the memory device 200c. The memory controller 100c may exchange data with the memory device 200c. The clock signal CK, the data clock signal WCK, and data are similar to the clock signal CK, the data clock signal WCK, and the data in FIG. 1, and thus, additional description will be omitted to avoid redundancy.

The memory device 200c may receive the command CMD and the address ADD from the memory controller 100c. The command CMD includes CMD_R1 and CMD_R2. CMD_R1 may indicate a command to be performed in the first memory rank 240a. CMD_R2 may indicate a command to be performed in the second memory rank 240b. CS_R1 may indicate a signal indicating whether to select the first memory rank 240a. CS_R2 may indicate a signal indicating whether to select the second memory rank 240b.

The I/O control circuit 230 may control the first memory rank 240a based on CS_R1 and CMD_R1. For example, the I/O control circuit 230 may select the first memory rank 240a based on CS_R1, and based on CMD_R1, the I/O control circuit 230 may write data in the first memory rank 240a or may read data from the first memory rank 240a.

The I/O control circuit 230 may control the second memory rank 240b based on CS_R2 and CMD_R2. For example, the I/O control circuit 230 may select the second memory rank 240b based on CS_R2, and based on CMD_R2, the I/O control circuit 230 may write data in the second memory rank 240b or may read data from the second memory rank 240b.

In an embodiment, the I/O control circuit 230 independently controls the first memory rank 240a and the second memory rank 240b. For example, while the I/O control circuit 230 writes data in the first memory rank 240a, the I/O control circuit 230 may read data from the second memory rank 240b. Alternately, while the I/O control circuit 230 writes data in the second memory rank 240b, the I/O control circuit 230 may read data from the first memory rank 240a.

Figure 11A:
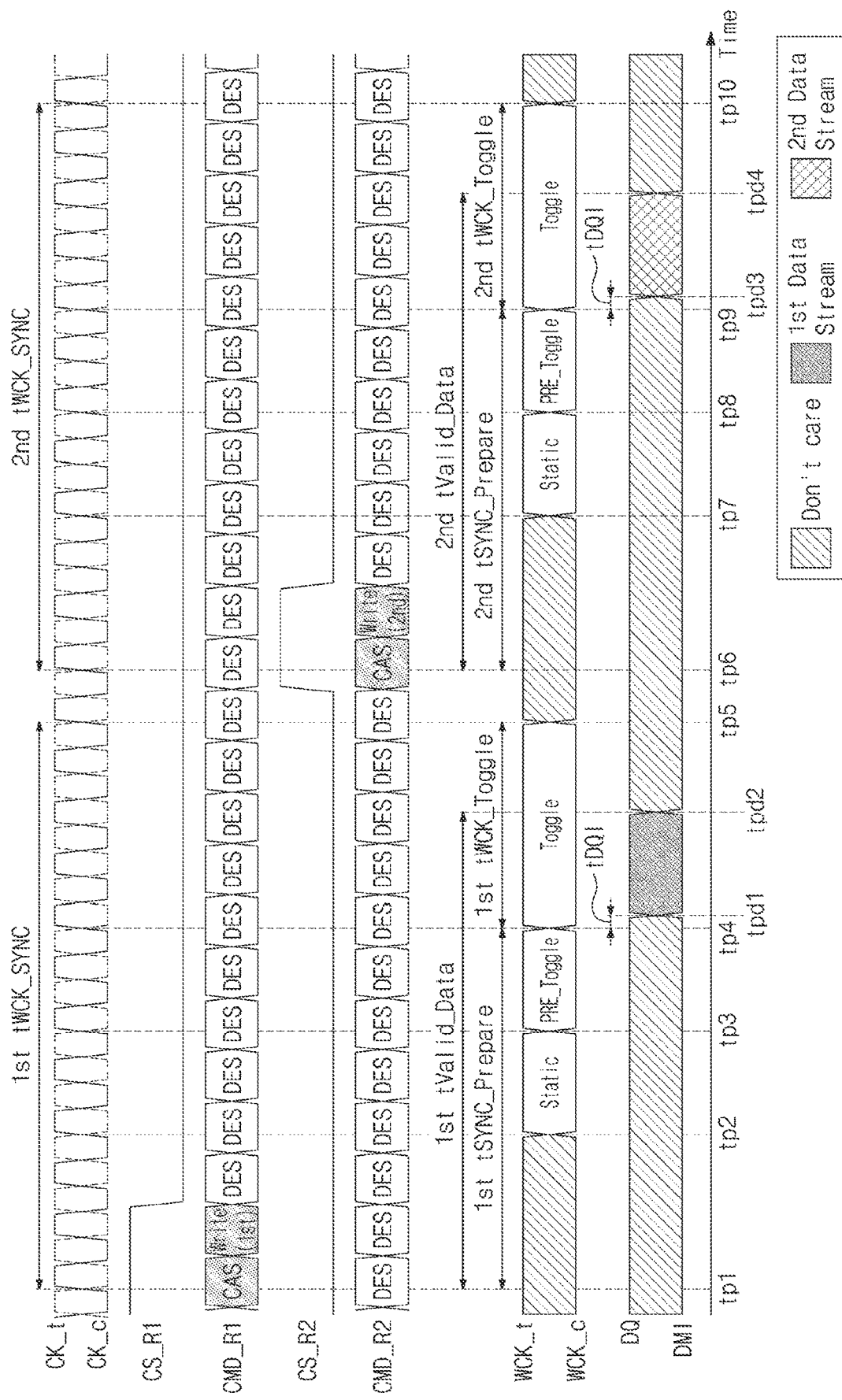
FIG. 11A is a timing diagram illustrating data streams that are processed according to an embodiment of the present disclosure.

FIG. 11A is a timing diagram illustrating data streams that are processed according to an embodiment of the present disclosure. A method for processing a plurality of data streams in a memory device where the synchronization of the data clock signal WCK is not extended will be described with reference to FIG. 11A.

Referring to FIG. 11A, waveforms of CK_t, CK_c, CS_R1, CMD_R1, CS_R2, CMD_R2, WCK_t, WCK_c, DQ, and DMI are illustrated by way of example. In FIG. 11A, a horizontal axis represents a time. In CK_t, CK_c, WCK_t, WCK_c, DQ, and DMI, meanings and a correspondence relationship with a memory device are similar to those described with reference to FIG. 4A, and CS_R1, CMD_R1, CS_R2, and CMD_R2 are similar to those described with reference to FIG. 10. Thus, additional description will be omitted to avoid redundancy. The timing diagram of FIG. 11A will be described with reference to FIGS. 10 and 11A.

The memory device 200c may process the first data stream through the first memory rank 240a and may process the second data stream through the second memory rank 240b. For example, the memory device 200c may process the first data stream during the time period 1st tWCK_SYNC. Afterwards, the memory device 200c may process the second data stream during the time period 2nd tWCK_SYNC.

At time tp4, the memory device 200c may allow the data clock signal WCK to toggle at the reference frequency. After the time period 1st tWCK_Toggle passes from time tp4, the synchronization of the data clock signal WCK may be disabled at time tp5. After the synchronization of the data clock signal WCK is disabled, processing of the second data stream may be requested. To again perform the synchronization of the data clock signal WCK, the memory device 200c may again prepare the toggling of the data clock signal WCK during the preparation time period 2nd tSYNC_Prepare, based on a new CAS (e.g., the CAS determined at time tp6). As such, processing of the second data stream may be delayed.

Figure 11B:
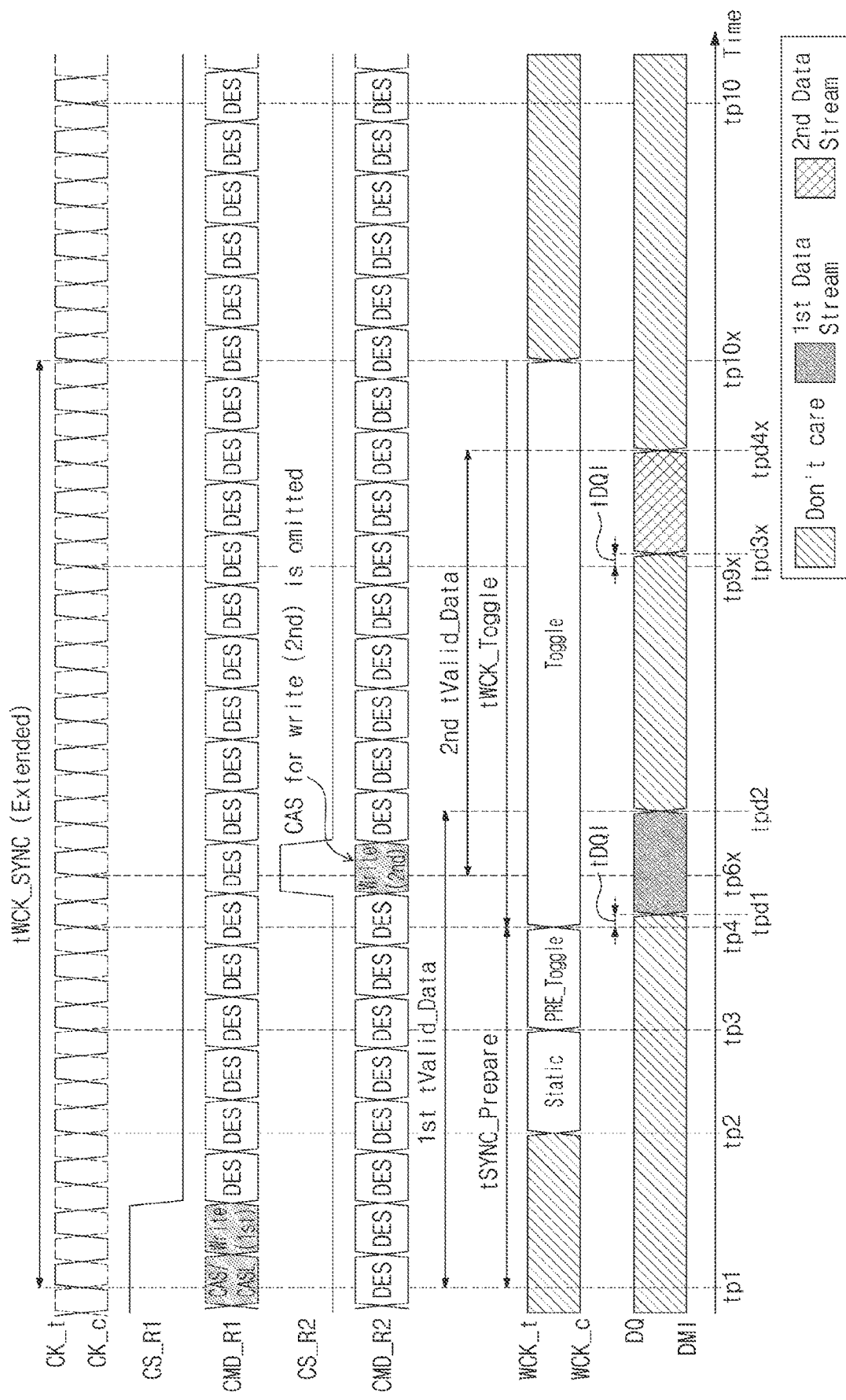
FIG. 11B is a timing diagram illustrating data streams that are processed based on a data clock signal in which synchronization is extended, according to an embodiment of the present disclosure.

FIG. 11B is a timing diagram illustrating data streams that are processed based on a data clock signal in which synchronization is extended, according to an embodiment of the present disclosure. A method for processing a plurality of data streams in a memory device where the synchronization of the data clock signal WCK is extended will be described with reference to FIG. 11B.

Referring to FIG. 11B, waveforms of CK_t, CK_c, CS_R1, CMD_R1, CS_R2, CMD_R2, WCK_t, WCK_c, DQ, and DMI are illustrated by way of example. In each waveform, the meaning and a correspondence relationship of a memory device are similar to those described with reference to FIG. 11A, and thus, additional description will be omitted to avoid redundancy. The timing diagram of FIG. 11B will be described with reference to FIGS. 10 and 11B.

In an embodiment, at time tp1, a command may be determined as the CASL. In an embodiment, the command CMD for changing settings of a mode register before time tp1 may be received, and the number of times that the data clock signal WCK toggles may be determined as the reference cycle count (or number) (e.g., greater than the default cycle count (or number)). At time tp1, a command may be determined as the CAS. As such, the synchronization of the data clock signal WCK of the memory device 200c may be extended. For example, the time period tWCK_Toggle corresponding to the synchronization of the data clock signal WCK may be from tp4 to tp10x, and the time period tWCK_Toggle may be longer than the time period 1st tWCK_Toggle in FIG. 11A.

In an embodiment, the memory device 200c processes the first data stream and the second data stream in parallel, based on the extended synchronization of the data clock signal WCK. For example, the memory device 200c may process the first data stream during the time period 1st tValid_Data. Before the processing of the first data stream is completed, at time tp6x, the memory device 200c may determine a write command for the second data stream. In this case, because the toggling of the data clock signal WCK is maintained, the memory device 200c may process the second data stream without the CAS for a write operation of the second data stream. At time tpd4x, the memory device 200c may complete the processing of the second data stream based on the toggling of the data clock signal WCK thus extended.

As described above, the memory device 200c may process the first data stream and the second data stream in parallel based on the extended synchronization of the data clock signal WCK, thus improving a data processing speed. For example, a time tpd4x when the processing of the second data stream is completed may be earlier than a time tpd4 of FIG. 11A, at which the processing of the second data stream is completed.

Figure 12A:
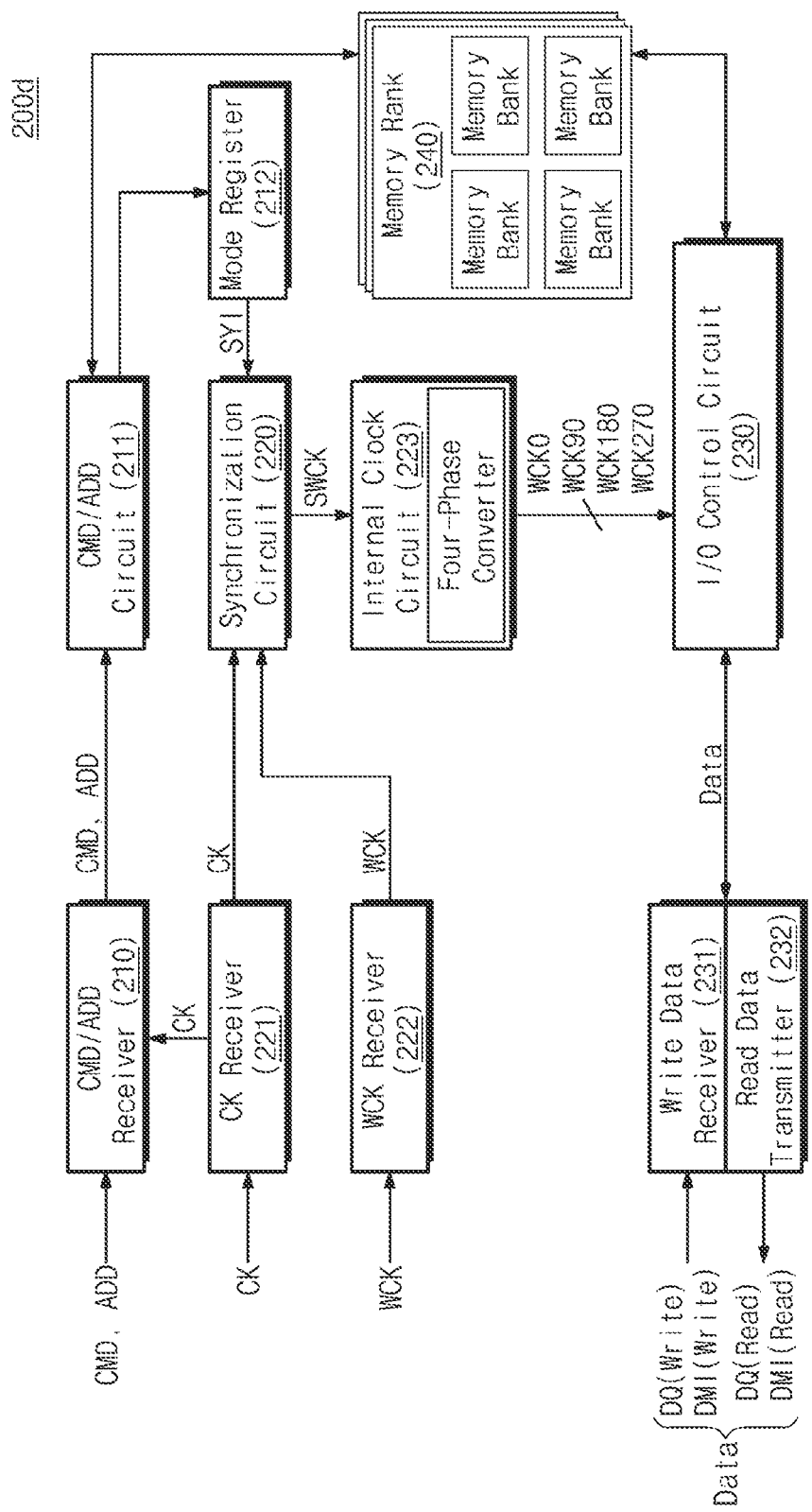
FIG. 12A is a block diagram illustrating a memory device according to an embodiment of the present disclosure.

FIG. 12A is a block diagram illustrating a memory device according to an embodiment of the present disclosure. Referring to FIG. 12A, a memory device 200d includes the CMD/ADD receiver 210, the CMD/ADD circuit 211, the mode register 212, the synchronization circuit 220, the CK receiver 221, the WCK receiver 222, the internal clock circuit 223, the I/O control circuit 230, the write data receiver 231, the read data transmitter 232, and the plurality of memory ranks 240.

The CMD/ADD receiver 210, the CMD/ADD circuit 211, the mode register 212, the synchronization circuit 220, the CK receiver 221, the WCK receiver 222, the I/O control circuit 230, the write data receiver 231, the read data transmitter 232, and the plurality of memory ranks 240 are similar to those described with reference to FIG. 3, and thus, additional description will be omitted to avoid redundancy.

In an embodiment, the internal clock circuit 223 may receive the synchronized data clock signal SWCK from the synchronization circuit 220. The internal clock circuit 223 may output an internal clock signal to the I/O control circuit 230 based on the synchronized data clock signal SWCK.

In an embodiment, the internal clock signal is a four-phase clock signal. For example, the internal clock circuit 223 may include a four-phase converter. The four-phase converter may generate a four-phase clock signal based on the synchronized data clock signal SWCK. The four-phase clock may include a first phase clock signal WCK0, a second phase clock signal WCK90, a third phase clock signal WCK180, and a fourth phase clock signal WCK270.

Phases of the first to fourth phase clock signals WCK0, WCK90, WCK180, and WCK270 may be different from one another. For example, a phase of the first phase clock signal WCK0 may be the same as a phase of the synchronized data clock signal SWCK. A phase of the second phase clock signal WCK90 may be delayed with respect to the phase of the synchronized data clock signal SWCK by as much as 90 degrees. A phase of the third phase clock signal WCK180 may be delayed with respect to the phase of the synchronized data clock signal SWCK by as much as 180 degrees. A phase of the fourth phase clock signal WCK270 may be delayed with respect to the phase of the synchronized data clock signal SWCK by as much as 270 degrees.

The first to fourth phase clock signals WCK0, WCK90, WCK180, and WCK270 may be used to process different data. For example, when processing of a data stream including first to fourth data is requested, the memory device 200d may process the first data of the data stream based on the first phase clock signal WCK0. The memory device 200d may process the second data of the data stream based on the second phase clock signal WCK90. The memory device 200d may process the third data of the data stream based on the third phase clock signal WCK180. The memory device 200d may process the fourth data of the data stream based on the fourth phase clock signal WCK270.

Figure 12B:
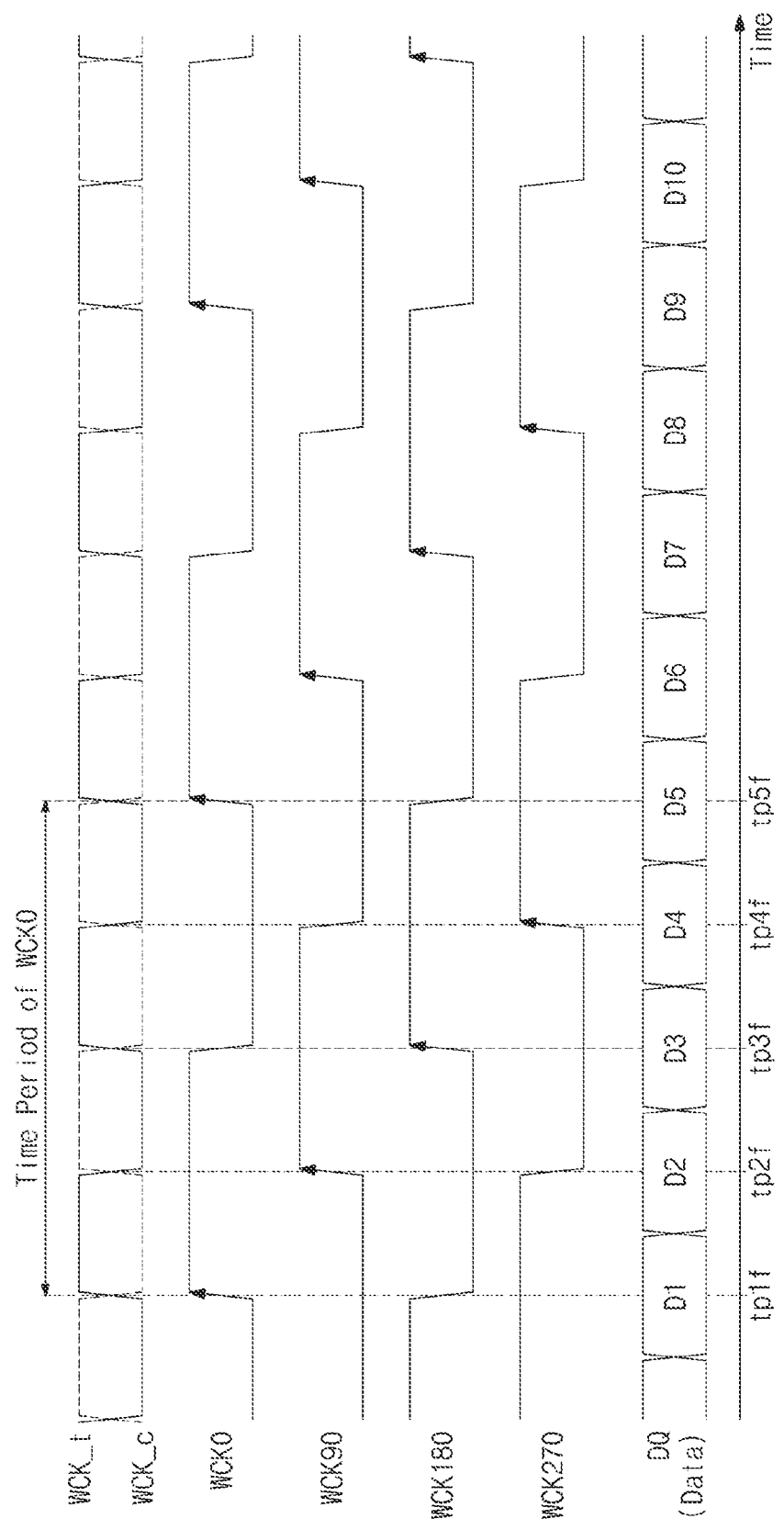
FIG. 12B is a timing diagram illustrating data clock signals and a data signal of FIG. 12A, according to an embodiment of the present disclosure.

FIG. 12B is a timing diagram illustrating data clock signals and a data signal of FIG. 12A, according to an embodiment of the present disclosure. Referring to FIG. 12B, waveforms of WCK_t, WCK_c, WCK0, WCK90, WCK180, WCK270, and DQ are illustrated by way of example. In FIG. 12B, a horizontal axis represents a time. WCK_t and WCK_c may correspond to the data clock signal WCK or the synchronized data clock signal SWCK of FIG. 12A. WCK0, WCK90, WCK180, and WCK270 may correspond to the first to fourth phase clock signals WCK0, WCK90, WCK180, and WCK270 of FIG. 12A, respectively. DQ may correspond to data DQ for a write operation of FIG. 12A or data DQ for a read operation of FIG. 12A. DQ may indicate a data stream including a plurality of data D1 to D10.

Referring to FIGS. 12A and 12B, the memory device 200d may generate the first to fourth phase clock signals WCK0, WCK90, WCK180, and WCK270 based on the synchronized data clock signal SWCK. The first to fourth phase clock signals WCK0, WCK90, WCK180, and WCK270 may have phase differences of 0 degree, 90 degrees, 180 degrees, and 270 degrees with respect to the synchronized data clock signal SWCK. Cycles (or periods) of the first to fourth phase clock signals WCK0, WCK90, WCK180, and WCK270 may be the same. For example, a cycle may correspond to a time period from tp1f to tp5f.

At time tp1f, the memory device 200d may process the first data D1 of the data stream corresponding to the DQ in response to a rising edge of the first phase clock signal WCK0. The rising edge may mean that a logical state of a clock signal changes from logical low to logical high. At time tp2f, the memory device 200d may process the second data D2 of the data stream corresponding to the DQ in response to a rising edge of the second phase clock signal WCK90. At time tp3f, the memory device 200d may process the third data D3 of the data stream corresponding to the DQ in response to a rising edge of the third phase clock signal WCK180. At time tp4f, the memory device 200d may process the fourth data D4 of the data stream corresponding to the DQ in response to a rising edge of the fourth phase clock signal WCK270.

Figure 13:
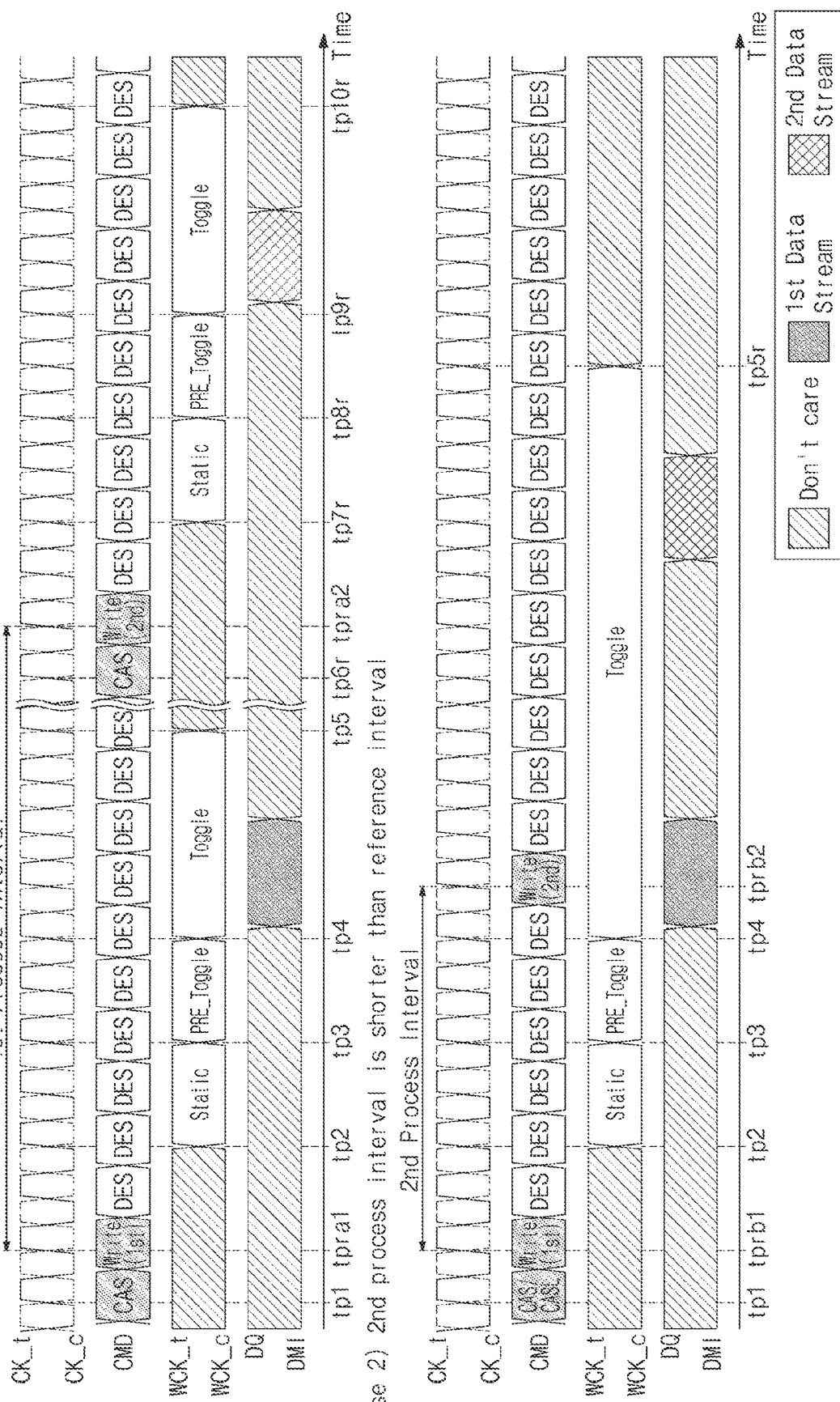
FIG. 13 is a timing diagram illustrating data streams that are processed based on a data clock signal selectively extended, according to an embodiment of the present disclosure.

FIG. 13 is a timing diagram illustrating data streams that are processed based on a data clock signal selectively extended, according to an embodiment of the present disclosure. A graph of data streams that are processed when a processing interval is longer than or equal to a reference interval is illustrated in FIG. 13. Also, a graph of data streams that are processed when the processing interval is shorter than the reference interval is illustrated.

The processing interval may mean a time interval between processing commands (e.g., read commands or write commands). The reference interval may be a time interval being a reference for determining whether to extend synchronization of a data clock signal. In each time and each waveform, the meaning and a correspondence relationship of a memory device are similar to those described with reference to FIGS. 4A and 9, and thus, additional description will be omitted to avoid redundancy.

According to an embodiment of the present disclosure, an electronic device may include a memory device and a memory controller controlling the memory device. The memory controller may include information about a time interval (i.e., a processing interval) between consecutive processing commands.

In an embodiment, when the processing interval is longer than or equal to the reference interval, the memory controller may determine that it is inefficient to extend the synchronization of the data clock signal. For example, when the processing interval is longer than or equal to the reference interval, the memory controller may determine that the extension of the synchronization of the data clock signal causes an increase in power consumption due to maintaining the synchronization of the data clock signal, rather than improving a data processing speed by omitting the CAS command.

In an embodiment, when the processing interval is shorter than the reference interval, the memory controller may determine that it is efficient to extend the synchronization of the data clock signal. For example, when the processing interval is shorter than the reference interval, the memory controller may determine that the extension of the synchronization of the data clock signal improves a data processing speed, rather than increasing power consumption due to maintaining the synchronization of the data clock signal.

In FIG. 13, referring to an embodiment of a first processing interval, the memory device may determine a first write command at time tpra1 and may determine a second write command at time tpra2. A time interval from time tpra1 when the first write command is determined to time tpra2 when the second write command is determined may be referred to as a "first processing interval". The memory controller may store information about the first processing interval.

In an embodiment, the memory controller determines whether the first processing interval is longer than or equal to the reference interval. When the first processing interval is longer than or equal to the reference interval, it may be inefficient to extend the synchronization of the data clock signal. The memory device does not extend the synchronization of the data clock signal under control of the memory controller. For example, at time tp5, the memory device 200 terminates the synchronization of the data clock signal WCK. A time interval from tp5 to tp6r may be long. At time tp6r, the memory device may determine the CAS command. At time tp9r, the memory device may again perform the synchronization of the data clock signal WCK.

In FIG. 13, referring to an embodiment of a second processing interval, the memory device may determine the first write command at time tprb1 and may determine the second write command at time tprb2. A time interval from time tprb1 when the first write command is determined to time tprb2 when the second write command is determined may be referred to as a "second processing interval". The memory controller may store information about the second processing interval.

In an embodiment, the memory controller determines whether the second processing interval is shorter than the reference interval. When the second processing interval is shorter than the reference interval, it may be efficient to extend the synchronization of the data clock signal. The memory device may extend the synchronization of the data clock signal under control of the memory controller.

For example, the memory controller may generate a command (e.g., the CASL) that indicates initiation of the synchronization of the data clock signal and defines a clock section corresponding to the synchronization. Alternatively, the memory controller may generate a command including mode register setting information for changing the number of times of toggling of the data clock signal to the reference cycle count (or number). The number of times of toggling of the data clock signal may be changed to the reference cycle count (or number). As such, the data clock signal may continuously toggle from time tp4 to time tp5r. For better understanding of the present disclosure, the processing interval may be illustrated as being between the first write command and the second write command, but the present disclosure is not limited thereto. For example, the first write command may be changed to a first read command, and the second write command may be changed to a second read command.

Figure 14:
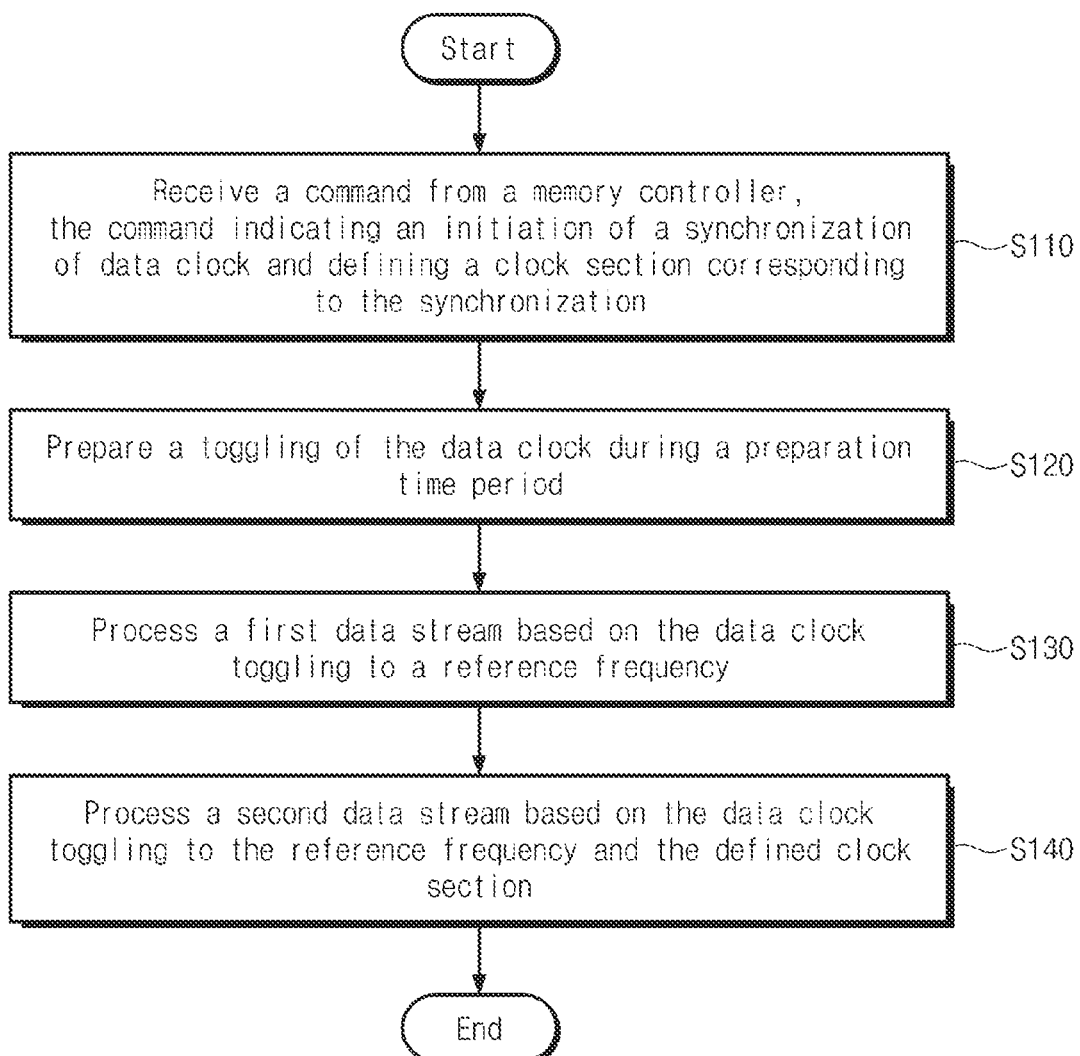
FIG. 14 is a flowchart illustrating an operating method of a memory device according to an embodiment of the present disclosure.

FIG. 14 is a flowchart illustrating an operating method of a memory device according to an embodiment of the present disclosure. An operating method of a memory device will be described with reference to FIG. 14. The memory device may correspond to at least one of the memory device 200 of FIG. 3, the memory device 200a of FIG. 5, the memory device 200c of FIG. 10, and the memory device 200d of FIG. 12A. The memory device may communicate with a memory controller.

In operation S110, the memory device may receive a command from the memory controller. The command may define a clock section that indicates initiation of synchronization of a data clock signal and corresponds to the synchronization. For example, the command may be the CASL being a defined command.

In an embodiment, the clock section defined by the command in operation S110 is longer than a clock section corresponding to the synchronization of the data clock signal, which is performed based on the CAS command in the LPDDR5.

In an embodiment, in operation S110, after receiving the command indicating the initiation of the synchronization of the data clock signal and defining the clock section, the memory device further receives a first processing command for processing a first data stream and a second processing command for processing a second data stream. For example, the first processing command may be a write command or a read command for the first data stream. The second processing command may be a write command or a read command for the second data stream. In an embodiment, a command received immediately before the second processing command is not the CAS and is not the CASL.

In operation S120, the memory device prepares toggling of the data clock signal during a preparation time period. In an embodiment, the preparation time period sequentially includes a first time period in which the data clock signal is in the don't care state, a second time period in which the data clock signal is maintained in a given logical state, and a third time period in which the data clock signal pre-toggles at a frequency lower than a reference frequency. The pre-toggling of the data clock signal may be performed by toggling the data clock signal at the frequency lower than the reference frequency.

In operation S130, the memory device processes the first data stream based on the data clock signal toggling at the reference frequency. In an embodiment, the memory device allows the data clock signal to toggle at the reference frequency during a fourth time period and then processes the first data stream. In an embodiment, the memory device generates a four-phase clock signal based on the data clock signal and processes the first data stream based on the four-phase clock signal.

In operation S140, the memory device processes the second data stream based on the data clock signal toggling at the reference frequency and the defined clock section. For example, unlike operation S130 in which the first data stream is processed, the second data stream may be processed within a time period where the synchronization of the data clock signal is extended by the CASL.

In an embodiment, the memory device allows the data clock signal to toggle at the reference frequency during a fifth time period and then processes the second data stream. In an embodiment, the memory device generates the four-phase clock signal based on the data clock signal and then processes the second data stream based on the four-phase clock signal. In this case, the four-phase clock signal may continuously toggle from when the first data stream is processed in operation S130 to when the second data stream is processed.

In an embodiment, the memory device processes a plurality of data streams through a plurality of memory ranks. For example, in operation S130, the memory device may process the first data stream through a first memory rank. In operation S140, the memory device may process the second data stream through a second memory rank. In this case, a time at which the processing of the second data stream starts may be earlier than a time at which the processing of the first data stream is completed.

Figure 15:
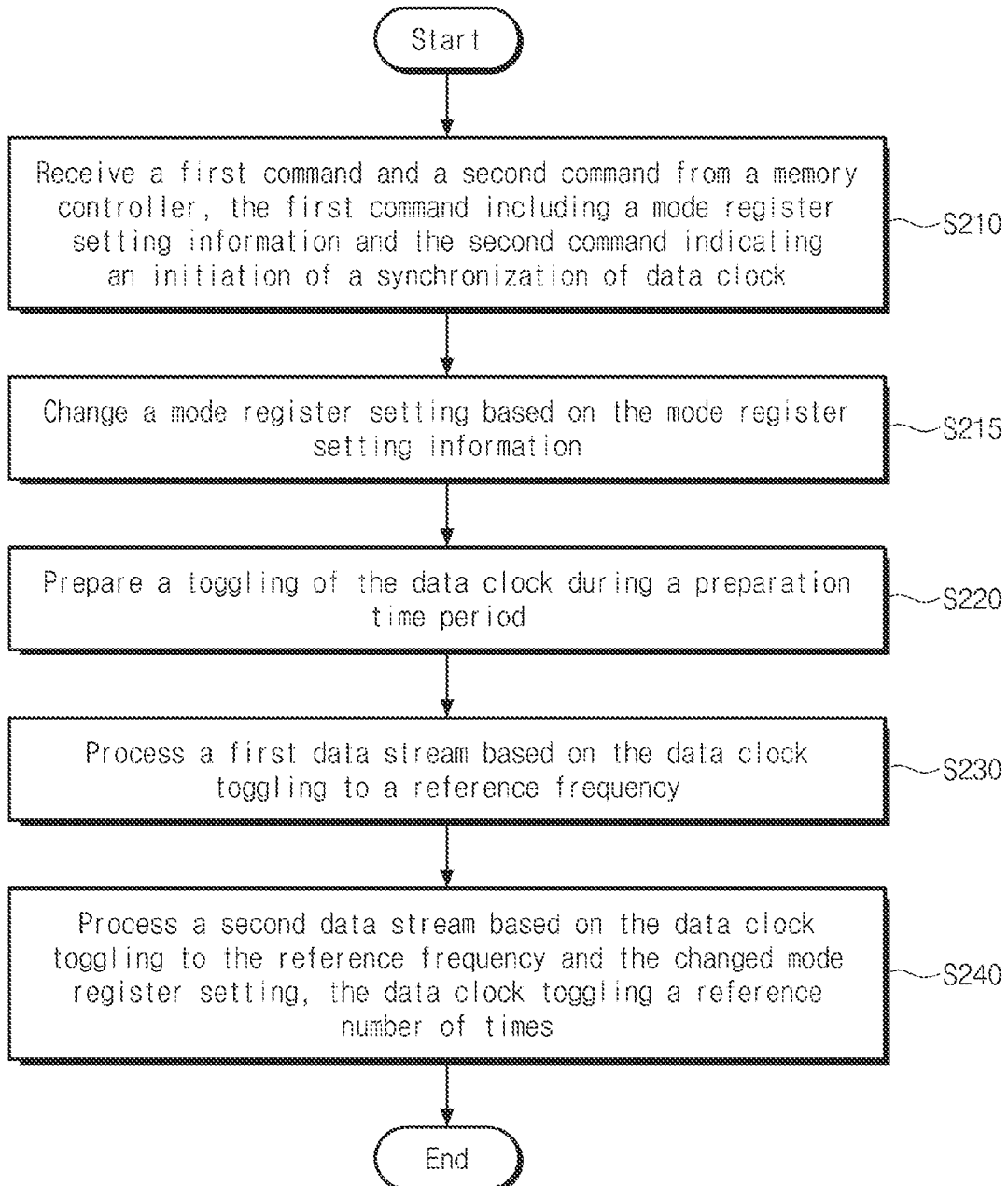
FIG. 15 is a flowchart illustrating an operating method of a memory device according to an embodiment of the present disclosure.

FIG. 15 is a flowchart illustrating an operating method of a memory device according to some embodiments of the present disclosure. An operating method of a memory device will be described with reference to FIG. 15. The memory device may correspond to at least one of the memory device 200 of FIG. 3, the memory device 200*b* of FIG. 7, the memory device 200*c* of FIG. 10, and the memory device 200*d* of FIG. 12A. The memory device may communicate with a memory controller.

In operation S210, the memory device receives a first command and a second command from the memory controller. The first command includes mode register setting information. The second command indicates initiation of synchronization of a data clock signal. For example, the first command may include the mode register setting information for extending the synchronization of the data clock signal. The second command may be the CAS command in the LPDDR5.

In an embodiment, in operation S210, after receiving the first command and the second command, the memory device may further receive a first processing command for processing a first data stream and a second processing command for processing a second data stream. In an embodiment, a command received immediately before the second processing command is not the CAS and is not the CASL.

In operation S215, the memory device changes settings of a mode register based on the mode register setting information. For example, the memory device may decode the first command received in operation S210 to obtain the mode register setting information. Based on the mode register setting information, the memory device may determine the number of times that the data clock signal toggles with regard to the synchronization, as a reference cycle count (or number). In this case, the reference cycle count (or number) may be greater than a default cycle count (or number) by which the data clock toggles, which is defined in the LPDDR5.

In operation S220, the memory device prepares toggling of the data clock signal during a preparation time period. In an embodiment, the preparation time period sequentially includes a first time period in which the data clock signal is in the don't care state, a second time period in which the data clock signal is maintained in a given logical state, and a third time period in which the data clock signal pre-toggles at a frequency lower than a reference frequency.

In operation S230, the memory device processes the first data stream based on the data clock signal toggling at the reference frequency. In an embodiment, the memory device allows the data clock signal to toggle at the reference frequency during a fourth time period and then processes the first data stream. In an embodiment, the memory device generates a four-phase clock signal based on the data clock signal and processes the first data stream based on the four-phase clock signal.

In operation S240, the memory device processes the second data stream based on the data clock signal toggling at the reference frequency and the changed settings of the mode register. For example, unlike operation S230 in which the first data stream is processed, the second data stream may be processed within a time period that is extended based on the changed settings of the mode register.

In an embodiment, the memory device allows the data clock signal to toggle at the reference frequency during a fifth time period and then processes the second data stream. In an embodiment, the memory device generates the four-phase clock signal based on the data clock signal and processes the second data stream based on the four-phase clock signal. In an embodiment, the memory device processes a plurality of data streams through a plurality of memory ranks.

Figure 16:
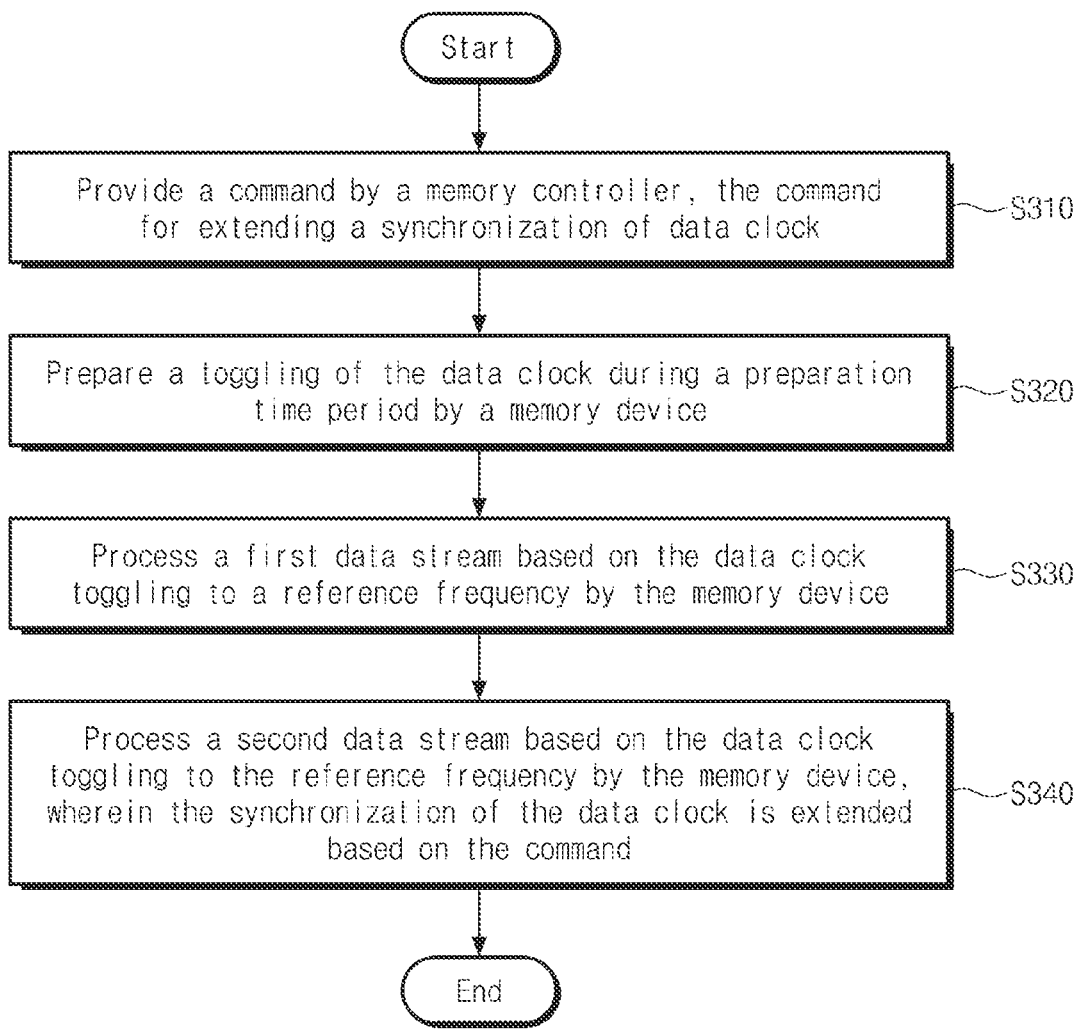
FIG. 16 is a flowchart illustrating an operating method of an electronic device according to an embodiment of the present disclosure.

FIG. 16 is a flowchart illustrating an operating method of an electronic device according to an embodiment of the present disclosure. The operating method of the electronic device will be described with reference to FIG. 16. The electronic device may include a memory controller and a memory device. The electronic device may correspond to at least one of the electronic device 10 of FIG. 1, the electronic device 20 of FIG. 5, the electronic device 30 of FIG. 7, the electronic device 40 of FIG. 10, and an electronic device including the memory device 200*d* of FIG. 12A.

In operation S310, the memory controller of the electronic device issues a command. The command is for extending synchronization of a data clock signal. For example, the command may be the CASL being a defined command. Alternatively, the command may include mode register setting information for extending the synchronization of the data clock signal.

In operation S320, the memory device of the electronic device prepares a toggling of the data clock signal during a preparation time period. In operation S330, the memory device of the electronic device processes a first data stream based on the data clock signal toggling at the reference frequency. In operation S340, the memory device of the electronic device processes a second data stream based on the data clock signal toggling at the reference frequency. A time at which the second data stream is processed may be included in a synchronization period of the data clock signal that is extended based on the command in operation S310.

Figure 17:
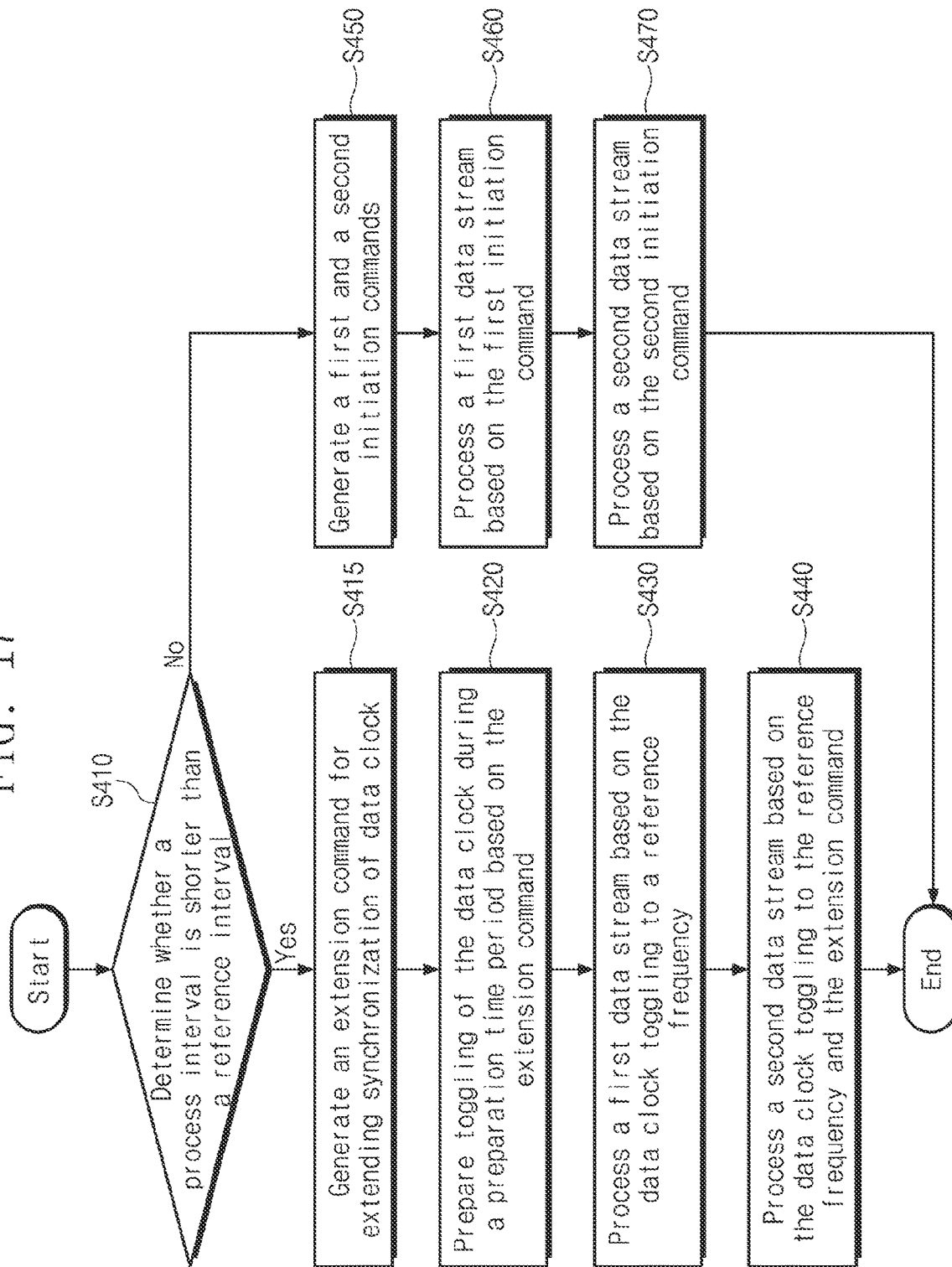
FIG. 17 is a flowchart illustrating an operating method of an electronic device according to an embodiment of the present disclosure.

FIG. 17 is a flowchart illustrating an operating method of an electronic device according to an embodiment of the present disclosure. The operating method of the electronic device will be described with reference to FIG. 17. The electronic device may include a memory controller and a memory device. The electronic device may correspond to at least one of the electronic device 10 of FIG. 1, the electronic device 20 of FIG. 5, the electronic device 30 of FIG. 7, the electronic device 40 of FIG. 10, and an electronic device including the memory device 200d of FIG. 12A. As in the embodiment of FIG. 13, the electronic device may compare a processing interval and a reference interval to determine whether to extend synchronization of a data clock signal.

In operation S410, the electronic device determines whether the processing interval is shorter than the reference interval. For example, a memory controller of the electronic device may determine whether a processing interval between a first processing command and a second processing command is shorter than the reference interval.

The first processing command may be a first read command for a first data stream or a first write command for the first data stream. The second processing command may be a second read command for a second data stream or a second write command for the second data stream. The reference interval may be a time interval being a reference for determining whether to extend the synchronization of the data clock signal.

When it is determined in operation S410 that the processing interval is shorter than the reference interval, the electronic device performs operation S415. In operation S415, the memory controller of the electronic device generates an extension command for extending the synchronization of the data clock signal.

In an embodiment, the extension command is a defined command (e.g., the CASL). For example, the defined command may indicate the initiation of the synchronization of the data clock signal and may define a clock section that corresponds to the synchronization.

In an embodiments, the extension command includes a mode register change command including mode register setting information and an initiation command (e.g., the CAS in the LPDDR5) indicating the initiation of the synchronization of the data clock signal.

In operation S420, the memory device of the electronic device prepares toggling of the data clock signal during a preparation time period, based on the extension command. In operation S430, the memory device processes the first data stream corresponding to the first processing command based on the data clock signal toggling at the reference frequency. In operation S440, the memory device of the electronic device processes the second data stream corresponding to the second processing command based on the data clock signal toggling at the reference frequency. In this case, the toggling of the data clock signal may be extended based on the extension command in operation S415, and the toggling of the data clock signal may be continuously maintained while both the first data stream and the second data stream are processed.

When it is determined in operation S410 that the processing interval is longer than or equal to the reference interval, the electronic device performs operation S450. In operation S450, the memory controller of the electronic device generates a first initiation command and a second initiation command. For example, the first initiation command may be a command indicating the initiation of the synchronization of the data clock signal for the purpose of processing the first processing command. The second initiation command may be a command indicating the initiation of the synchronization of the data clock signal for the purpose of processing the second processing command. In an embodiment, each of the first initiation command and the second initiation command are the CAS command in the LPDDR5.

In operation S460, the memory device of the electronic device processes the first data stream based on the first initiation command. For example, the memory device of the electronic device may process the first data stream corresponding to the first processing command based on the data clock signal toggling based on the first initiation command.

In an embodiment, operation S460 may include preparing, by the memory device, toggling of the data clock signal during a preparation time period based on the first initiation command, processing, by the memory device, the first data stream based on the data clock signal toggling at the reference frequency, and terminating, by the memory device, the toggling of the data clock signal after the processing of the first data stream (i.e., terminating the synchronization of the data clock signal).

In operation S470, the memory device of the electronic device processes the second data stream based on the second initiation command. For example, the memory device of the electronic device may process the second data stream corresponding to the second processing command based on the data clock signal toggling based on the second initiation command. In this case, unlike the case of processing the second data stream in operation S440, after toggling is terminated in operation S460, the data clock signal in operation S470 may again toggle based on the second initiation command.

In an embodiment, operation S470 include preparing, by the memory device, toggling of the data clock signal during a preparation time period based on the second initiation command, processing, by the memory device, the second data stream based on the data clock signal toggling at the reference frequency, and terminating, by the memory device, the toggling of the data clock signal after the processing of the second data stream (i.e., terminating the synchronization of the data clock signal).

Figure 18:
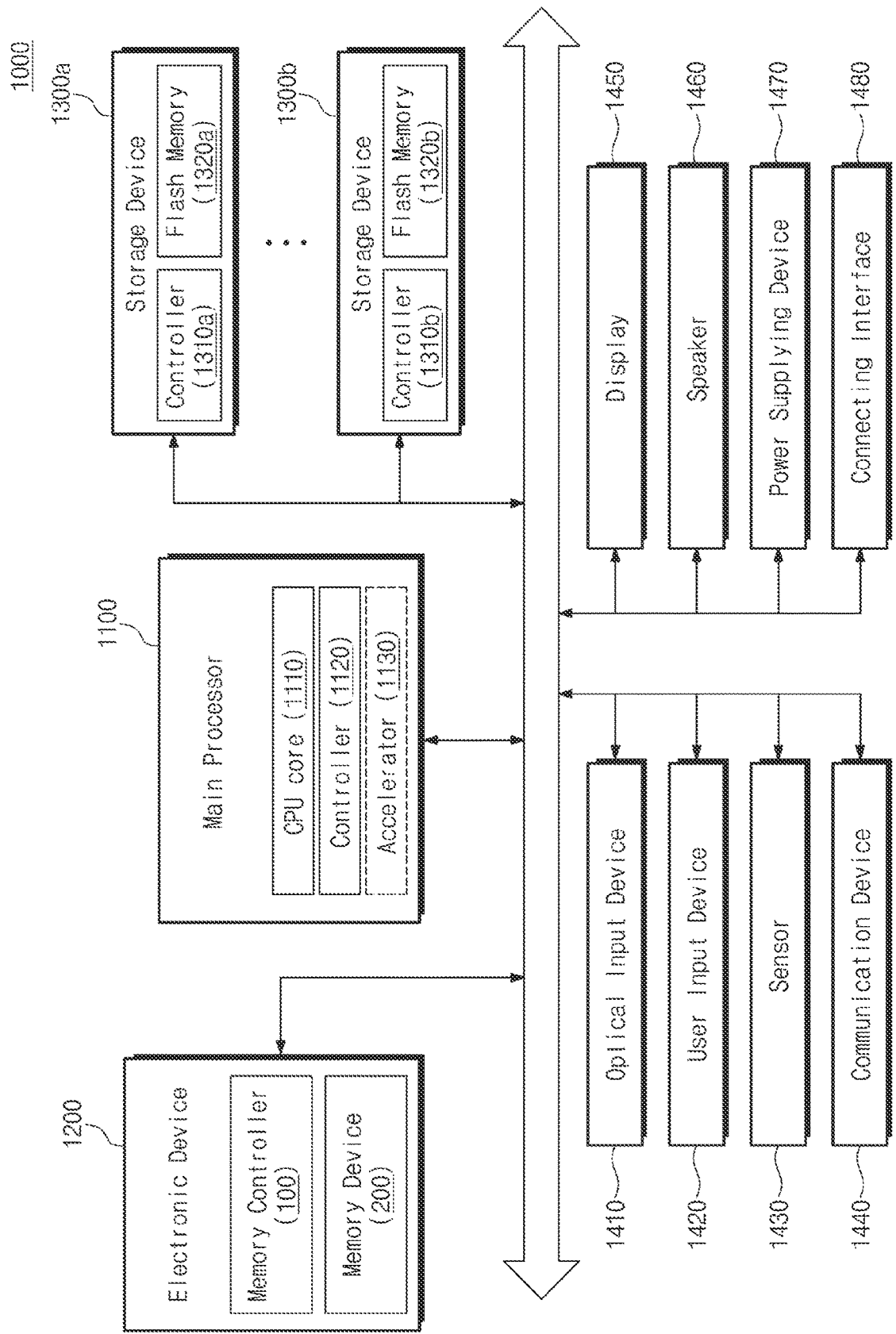
FIG. 18 is a block diagram illustrating an electronic system according to an embodiment of the present disclosure.

FIG. 18 is a block diagram illustrating an electronic system according to an embodiment of the present disclosure. Referring to FIG. 18, an electronic system 1000 includes an electronic device 1200. The electronic device 1200 may correspond to at least one of the electronic device 10 of FIG. 1, the electronic device 20 of FIG. 5, the electronic device 30 of FIG. 7, the electronic device 40 of FIG. 10, and an electronic device including the memory device 200d of FIG. 12A. An operating method of the electronic device 1200 may correspond to the flowchart of FIG. 16. The electronic device 1200 may include the memory device 200. An operating method of the memory device 200 may correspond to at least one of the flowchart of FIG. 14 and the flowchart of FIG. 15.

The electronic system 1000 may be a mobile system such as a mobile phone, a smartphone, a tablet PC, a wearable device, a health care device, or an Internet of things (IoT) device. However, the electronic system 1000 is not limited to the mobile system. For example, the electronic system 1000 may be a system such as a personal computer, a laptop, a server, a media player, or an automotive device such as a navigation device.

The electronic system 1000 may include a main processor 1100, the electronic device 1200, and storage devices 1300a and 1300b, and may further include one or more of an optical input device 1410, a user input device 1420, a sensor 1430, a communication device 1440, a display 1450, a speaker 1460, a power supplying device 1470, and a connecting interface 1480.

The main processor 1100 may control overall operations of the electronic system 1000. For example, the main processor 1100 may control operations of the remaining components of the electronic system 1000 implementing the electronic system 1000. The main processor 1100 may be implemented with a general-purpose processor, a special-purpose processor, or an application processor.

The main processor 1100 may include one or more CPU cores 1110, and may further include a controller 1120 for controlling the electronic device 1200 and/or the storage devices 1300a and 1300b. In some embodiments, the main processor 1100 may further include an accelerator 1130 being a dedicated circuit for high-speed data computation such as artificial intelligence (AI) data computation. The accelerator 1130 may include a graphics processing unit (GPU), a neural processing unit (NPU), and/or a data processing unit (DPU) and may be implemented with a separate chip physically independent of any other component of the main processor 1100.

The electronic device 1200 may be a volatile memory such as a DRAM and/or an SRAM. The electronic device 1200 may be implemented within the same package as the main processor 1100.

The storage devices 1300a and 1300b may function as a nonvolatile storage device that stores data regardless of whether power is supplied, and may have a relatively high capacity compared to the electronic device 1200. The storage device 1300a may include a storage controller 1310a and a flash memory 1320a storing data under control of the storage controller 1310a, and the storage device 1300b may include a storage controller 1310b and a flash memory 1320b storing data under control of the storage controller 1310b. Each of the flash memories 1320a and 1320b being non-volatile memories may include a flash memory of a two-dimensional (2D) structure or a V-NAND flash memory of a three-dimensional structure or may include a different kind of nonvolatile memory such as a PRAM and/or a RRAM.

The storage devices 1300a and 1300b may be included in the electronic system 1000 in a state of being physically separated from the main processor 1100 or may be implemented within the same package as the main processor 1100. Also, the storage devices 1300a and 1300b may have a shape identical to that of a solid state drive (SSD) or a memory card so as to be removable from any other components of the electronic system 1000 through an interface such as the connecting interface 1480 to be described later. The storage devices 1300a and 1300b may include a device to which the standard such as universal flash storage (UFS), embedded multi-media card (eMMC), or non-volatile memory express (NVMe) is applied, but is not limited thereto.

The optical input device 1410 may photograph (or capture) a still image or a moving image and may include a camera, a camcorder, and/or a webcam.

The user input device 1420 may receive various types of data input by a user of the electronic system 1000 and may include a touch pad, a keypad, a keyboard, a mouse, and/or a microphone.

The sensor 1430 may detect various types of physical quantities capable of being obtained from the outside of the electronic system 1000 and may convert the detected physical quantities to electrical signals. The sensor 1430 may include a temperature sensor, a pressure sensor, an illumination sensor, a position sensor, an acceleration sensor, a biosensor, and/or a gyroscope sensor.

The communication device 1440 may communicate with external devices of the electronic system 1000 in compliance with various communication protocols. The communication device 1440 may be implemented to include an antenna, a transceiver, and/or a MODEM.

The display 1450 and the speaker 1460 may function as an output device that outputs visual information and auditory information to the user of the electronic system 1000.

The power supplying device 1470 may appropriately convert a power supplied from a battery (not illustrated) embedded in the electronic system 1000 and/or an external power source so as to be supplied to each component of the electronic system 1000.

The connecting interface 1480 may provide a connection between the electronic system 1000 and an external device. The connecting interface 1480 may be implemented with various interfaces such as an ATA (Advanced Technology Attachment) interface, an SATA (Serial ATA) interface, an e-SATA (external SATA) interface, an SCSI (Small Computer Small Interface) interface, an SAS (Serial Attached SCSI) interface, a PCI (Peripheral Component Interconnection) interface, a PCIe (PCI express) interface, an NVMe (NVM express) interface, an IEEE 1394 interface, an USB (Universal Serial Bus) interface, an SD (Secure Digital) card interface, an MMC (Multi-Media Card) interface, an eMMC (embedded Multi-Media Card) interface, an UFS (Universal Flash Storage) interface, an eUFS (embedded Universal Flash Storage) interface, and a CF (Compact Flash) card interface.

According to at least one embodiment of the present disclosure, an operating method of a memory device for extending synchronization of a data clock signal, and an operating method of an electronic device including the memory device are provided.

Also, according to at least one embodiment of the present disclosure, since synchronization of a data clock signal is extended based on a defined command or a setting change of a mode register, a memory device is provided that is capable of skipping additional synchronization of the data clock signal and improving a data processing speed.

While the present disclosure has been described with reference to embodiments thereof, it will be apparent to those of ordinary skill in the art that various changes and modifications may be made thereto without departing from the spirit and scope of the present disclosure as set forth in the following claims.

What is claimed is:

1. A method of operating an electronic device which includes a memory device and a memory controller, the method comprising:
   determining, by the memory controller, whether a processing interval between a first processing command and a second processing command is shorter than a reference interval;
   providing, by the memory controller, in response to determining that the processing interval is shorter than the reference interval, a first command with the memory device based on a first mode, wherein the first mode indicates that a data clock signal of the memory device is continuously toggling for the first and second processing commands; and
   providing, by the memory controller, in response to determining that the processing interval is not shorter than the reference interval, a second command with the memory device based on a second mode different from the first mode.

2. The method of claim 1, further comprises:
toggling, by the memory device, the data clock signal based on the first command;
processing, by the memory device, a first data stream corresponding to the first processing command based on the toggled data clock signal; and
processing, by the memory device, a second data stream corresponding to the second processing command based on the toggled data clock signal, wherein the data clock signal is continuously toggling while processing the first and second data streams.

3. The method of claim 2, wherein the toggling, by the memory device, the data clock signal based on the first command comprises:
pre-toggling, by the memory device, the data clock signal at a pre-toggling frequency; and
toggling, by the memory device, the data clock signal at a reference frequency higher than the pre-toggling frequency.

4. The method of claim 3, wherein the pre-toggling frequency is lower than the reference frequency as much as two times.

5. The method of claim 1, further comprises:
toggling, by the memory device, the data clock signal based on the second command;
processing, by the memory device, a first data stream corresponding to the first processing command based on the toggled data clock signal; and
disabling, by the memory device, the toggled data clock signal before processing a second data stream corresponding to the second processing command.

6. The method of claim 5, wherein the disabling, by the memory device, the toggled data clock signal comprises:
stopping, by the memory device, the toggling of the data clock signal; or
maintaining, by the memory device, the data clock signal in a don care state.

7. The method of claim 5, further comprises:
providing, by the memory controller, a third command with the memory device after providing the second command;
re-toggling, by the memory device, the disabled data clock signal based on the third command;
processing, by the memory device, the second data stream corresponding to the second processing command based on the re-toggled data clock signal.

8. The method of claim 7, further comprises:
disabling, by the memory device, the re-toggled data clock signal after processing the second data stream.

9. The method of claim 1, wherein the first command includes mode register setting information.

10. The method of claim 9, further comprises:
changing, by the memory device, settings of a mode register based on the mode register setting information of the first command;
preparing, by the memory device, a toggling of the data clock signal during a preparation time period;
processing, by the memory device, a first data stream corresponding to the first data stream based on the data clock signal toggling at a reference frequency; and
processing, by the memory device, a second data stream corresponding to the second data stream based on the data clock signal toggling at the reference frequency and extended according to a reference cycle count of the changed settings.

11. The method of claim 10, wherein the changing, by the memory device, the settings of the mode register based on the mode register setting information of the first command comprises:
decoding, by the memory device, the first command to obtain the mode register setting information; and
determining, by the memory device, a number of times that the data clock signal toggles as a reference cycle count based on the mode register setting information, and
wherein the reference cycle count is greater than the number of times that the data clock signal toggles according to a low power double data rate 5 (LPDDR5).

12. The method of claim 10, wherein the preparation time period sequentially includes a first time period, a second time period, and a third time period,
wherein the preparing, by the memory device, the toggling of the data clock signal during the preparation time period comprises:
maintaining, by the memory device, the data clock signal in a don't care state during the first time period;
maintaining, by the memory device, the data clock signal in a given logical state during the second time period; and
toggling, by the memory device, the data clock signal at a pre-toggling frequency lower than the reference frequency during the third time period.

13. The method of claim 1, wherein the first command includes an initiation command indicating initiation of a toggling of the data clock signal and indicating a defined clock section, and
wherein a period of the defined clock section is longer than a period of a default clock section corresponding to a column address strobe (CAS) command in a low power double data rate 5 (LPDDR5).

14. The method of claim 1, wherein, in the first mode, the first and the second processing commands are processed based on one column address strobe (CAS) command, and
wherein, in the second mode, the first and the second processing commands are processed based on two column address strobe (CAS) commands.

15. The method of claim 1, wherein the memory device includes:
a first memory rank configured to store a first data stream corresponding to the first processing command; and
a second memory rank configured to store a second data stream corresponding to the second processing command.

16. An electronic device comprising:
a memory device configured to support a first mode and a second mode, process a first data stream based on a first processing command, and process a second data stream based on a second processing command; and
a memory controller configured to:
determine whether a processing interval between the first processing command and the second processing command is shorter than a reference interval;
provide, in response to determining that the processing interval is shorter than the reference interval, a first command with the memory device based on the first mode; and provide, in response to determining that the processing interval is not shorter than the reference interval, a second command with the memory device based on the second mode, and wherein the first mode indicates that a data clock signal of the memory device is continuously toggling for the first and second processing commands.

17. The electronic device of claim 16, wherein the memory device is further configured to:

toggle the data clock signal based on the first command;

process the first data stream corresponding to the first processing command based on the toggled data clock signal; and process the second data stream corresponding to the second processing command based on the toggled data clock signal, and wherein the data clock signal is continuously toggling while processing the first and second data streams.

18. The electronic device of claim 16, wherein the memory device is further configured to:

toggle the data clock signal based on the second command;

process the first data stream corresponding to the first processing command based on the toggled data clock signal; and disable the toggled data clock signal before processing the second data stream corresponding to the second processing command.

19. A method of operating an electronic device which includes a memory device and a memory controller, the method comprising:

determining, by the memory controller, whether a processing interval between a first processing command and a second processing command is shorter than a reference interval;

generating, by the memory controller, in response to determining that the processing interval is shorter than the reference interval, an extension command for extending a toggling of a data clock signal;

preparing, by the memory device, the toggling of the data clock signal during a preparation time period based on the extension command;

processing, by the memory device, a first data stream corresponding to the first processing command based on the data clock signal toggling at a reference frequency; and processing, by the memory device, a second data stream corresponding to the second processing command based on the data clock signal toggling at the reference frequency, wherein the toggling of the data clock signal is extended based on the extension command.

20. The method of claim 19, further comprises:

generating, by the memory controller, in response to determining that the processing interval is not shorter than the reference interval, a first initiation command indicating initiation of a first toggling of the data clock signal to processing the first processing command and a second initiation command indicating initiation of a second toggling of the data clock signal to processing the second processing command;

processing, by the memory device, the first data stream corresponding to the first processing command based on the first initiation command and the first processing command; and processing, by the memory device, the second data stream corresponding to the second processing command based on the second initiation command and the second processing command.

* * * * *